(12) United States Patent
Abe et al.

(10) Patent No.: US 10,914,725 B2
(45) Date of Patent: Feb. 9, 2021

(54) CULTURE MEDIUM ADDITIVE, CULTURE MEDIUM COMPOSITION, AND METHOD FOR CULTURING CELLS OR TISSUE USING SAME

(71) Applicant: NISSAN CHEMICAL INDUSTRIES, LTD., Tokyo (JP)

(72) Inventors: Natsuki Abe, Shiraoka (JP); Taito Nishino, Shiraoka (JP); Ayako Otani, Shiraoka (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 59 days.

(21) Appl. No.: 15/566,981

(22) PCT Filed: Apr. 15, 2016

(86) PCT No.: PCT/JP2016/062689
§ 371 (c)(1),
(2) Date: Oct. 16, 2017

(87) PCT Pub. No.: WO2016/167373
PCT Pub. Date: Oct. 20, 2016

(65) Prior Publication Data
US 2018/0136196 A1    May 17, 2018

(30) Foreign Application Priority Data

Apr. 16, 2015 (JP) ................. 2015-084590
Nov. 25, 2015 (JP) ................. 2015-229974

(51) Int. Cl.
| | | |
|---|---|---|
| C08L 5/12 | (2006.01) |
| C12N 5/00 | (2006.01) |
| G01N 33/50 | (2006.01) |
| C12Q 1/02 | (2006.01) |
| C08B 37/12 | (2006.01) |

(52) U.S. Cl.
CPC .......... *G01N 33/5011* (2013.01); *C08B 37/12* (2013.01); *C08L 5/12* (2013.01); *C12N 5/0018* (2013.01); *C12Q 1/02* (2013.01); *C12N 2533/76* (2013.01)

(58) Field of Classification Search
CPC .... C12N 5/067; C12N 5/0693; C12N 5/0018; C12N 2533/76; C08B 37/12; C08L 5/12
See application file for complete search history.

(56) References Cited

U.S. PATENT DOCUMENTS

| | | | |
|---|---|---|---|
| 2002/0085987 A1* | 7/2002 | Brown | A61K 8/11 424/70.11 |
| 2005/0090005 A1 | 4/2005 | Kojima et al. | |
| 2013/0029932 A1 | 1/2013 | Kachi et al. | |
| 2014/0106348 A1* | 4/2014 | Nishino | G01N 33/5044 435/6.11 |
| 2014/0248655 A1 | 9/2014 | Furukawa | |

FOREIGN PATENT DOCUMENTS

| | | |
|---|---|---|
| CN | 102892399 A | 1/2013 |
| EP | 2878664 A1 | 6/2015 |
| JP | H07-079772 A | 3/1995 |
| JP | 2004-141110 A | 5/2004 |
| JP | 2004-283073 A | 10/2004 |
| JP | 2009-229339 A | 10/2009 |
| JP | 2014-094001 A | 5/2014 |
| WO | WO 2011/111854 A1 | 9/2011 |
| WO | WO 2012/129538 A1 | 9/2012 |
| WO | WO 2013/051590 A1 | 4/2013 |
| WO | WO 2014/017513 A1 | 1/2014 |

OTHER PUBLICATIONS

Wikipedia, "Agar", https://en.wikipedia.org/wiki/Agar (Year: 2019).*
Ito et al., "Shinki Kanten no Kaihatsu Oyobi sono Tenkai ni Tsuite," *Gekkan Food Chemical*, 22(5): 40-44 (2006).
Longati et al., "3D pancreatic carcinoma spheroids induce a matrix-rich, chemoresistant phenotype offering a better model for drug testing," *BMC Cancer*, 13: 95 (2013).
Misawa, "Kanten no Kinosei to Shokuhin eno Oyo," *New Food Industry*, 56(8): 1-8 (2014).
Japanese Patent Office, International Search Report in International Patent Application No. PCT/JP2016/062689 (dated Jul. 12, 2016).
Fang et al., "Expansion of CD133+ colon cancer cultures retaining stem cell properties to enable cancer stem cell target discovery," *Br. J. Cancer*, 102(8): 1265-1275 (2010).
Fiebig et al., "Clonogenic assay with established human tumour xenografts: correlation of in vitro and in vivo activity as a basis for anticancer drug discovery," *Eur. J. Cancer*, 40(6): 802-820 (2004).
European Patent Office, Extended European Search Report in European Patent Application No. 16780164.6 (Oct. 12, 2018).
Abe-Fukasawa et al., "Novel 3D Liquid Cell Culture Method for Anchorage-independent Cell Growth, Cell Imaging and Automated Drug Screening," *Sci. Rep.*, 8(1): 3627 (2018).
Ramnani et al., "In vitro fermentation and prebiotic potential of novel low molecular weight polysaccharides from agar and alginate seaweeds," *Anaerobe*, 18(1): 1-6 (2012).

(Continued)

*Primary Examiner* — Ruth A Davis
(74) *Attorney, Agent, or Firm* — Leydig, Voit & Mayer, Ltd.

(57) ABSTRACT

The invention provides a medium additive, medium composition and a culture method and the like, capable of efficiently culturing cells or tissues in a well dispersed state, and further, permitting cell image analysis of the cells or tissues. The medium additive or medium composition contains agar, which preferably is a low molecular weight agar having a weight average molecular weight of 10,000-60,000. Using same, cells or tissues can be cultured in a well-dispersed state in a medium, and a proliferation promoting effect for the cells or tissues can also be obtained. In addition, the cells can be cultured in any of a floating state and a precipitated state by adjusting the concentration of the aforementioned agar.

6 Claims, 8 Drawing Sheets
(8 of 8 Drawing Sheet(s) Filed in Color)

(56) References Cited

OTHER PUBLICATIONS

European Patent Office, Communication Pursuant to Article 94(3) EPC in European Patent Application No. 16780164.6 (Jun. 4, 2019).
China National Intellectual Property Administration, The First Office Action in Chinese Patent Application No. 201680022581.3 (dated Mar. 24, 2020).

\* cited by examiner

HepG2 cells (photographed on day 7)

negative control    0.03% low-molecular agar

A549 cells (observed images by ArrayScan on day 10)

negative control     0.015% deacylated gellan gum     0.03% low-molecular agar low-molecular agar 0.03(w/v)%     agarose 0.03(w/v)% low melting point agarose 0.01(w/v)%     fast-dissolving agar 0.07(w/v)%

CULTURE MEDIUM ADDITIVE, CULTURE MEDIUM COMPOSITION, AND METHOD FOR CULTURING CELLS OR TISSUE USING SAME

CROSS-REFERENCE TO RELATED APPLICATIONS

This patent application is the U.S. national phase of International Patent Application No. PCT/JP2016/062689, filed on Apr. 15, 2016, which claims the benefit of Japanese Patent Application No. 2015-084590, filed on Apr. 16, 2015, and Japanse Patent Application No. 2015-229974, filed on Nov. 25, 2015, the disclosures of which are incorporated herein by reference in their entireties for all purposes.

TECHNICAL FIELD

The present invention relates to a medium additive and a medium composition, which make it possible to disperse cells or tissues well and culture them in a floating or sedimented state, and a method of culturing cells or tissues by using the medium additive or medium composition.

BACKGROUND ART

In recent years, techniques for proliferating or maintaining in vitro various organs, tissues and cells that play distinct roles in the body of animals and plants have been developed. Proliferation or maintenance of the organs and tissues in vitro is called organ culture and tissue culture, respectively, and proliferating, differentiating or maintaining in vitro the cells separated from an organ or tissue is called cell culture. Cell culture is a technique for proliferating, differentiating or maintaining separated cells in vitro in a medium, and is indispensable for detailed analyses of the in vivo function and structure of various organs, tissues and cells. In addition, the cells or tissues cultured by the technique are utilized in various fields for efficacy and toxicity evaluation of chemical substances, pharmaceutical products and the like, large-scale production of useful substances such as enzymes, cell growth factors, antibodies and the like, regenerative medicine supplementing organ, tissue and cell that were lost by disease and deficiency, improvement in plant varieties, production of genetically modified crops, and the like.

Animal-derived cells are broadly divided into two, floating cells and adherent cells, based on the properties thereof. Floating cells are cells that do not require a scaffold for growth and proliferation, and adherent cells are cells that require a scaffold for growth and proliferation. Most of the cells constituting the living body are the latter, adherent cells. As culture methods of adherent cells, single layer culture, dispersion culture, embedded culture, microcarrier culture, sphere culture and the like are known.

It has been reported that animal and plant cells and/or tissues can be cultured in suspension by uniformly dispersing them in a stationary state in a liquid medium mixed with a structure containing a polymer compound having an anionic functional group such as deacylated gellan gum and the like, without substantially increasing the viscosity of the liquid medium, and that the proliferation activity of the cell can be promoted by culturing in the medium composition (patent document 1). In addition, examples of promoting cell proliferation have also been reported in which a thickener such as methylcellulose and the like is used to disperse adherent cells and promote formation of spheroids (cell aggregates in which cells are assembled and aggregated, sometimes to be referred to as "sphere" in the present specification) (patent document 2, non-patent document 1).

DOCUMENT LIST

Patent Documents patent document 1: WO 2014/017513
patent document 2: JP-A-7-79772

Non-Patent Document non-patent document 1: Paola Longati et al., BMC Cancer 2013, 13:95

SUMMARY OF THE INVENTION

Problems to be Solved by the Invention

As mentioned above, patent document 1 reports that cells or tissues can be cultured in suspension by dispersing them well in a stationary state in a liquid medium mixed with a structure containing a polymer compound having an anionic functional group such as deacylated gellan gum and the like, without substantially increasing the viscosity of the liquid medium, and that the proliferation activity of the cell can be promoted by culturing in the medium composition. However, the present inventors have found a new problem in culturing cells or tissues by using the medium composition that cultures cannot be directly subjected to cell image analysis, because the cells or tissues in a floating state prevent focusing of the lens when they are analyzed with a cell imaging device.

The present invention aims to provide a medium composition and a culture method and the like, capable of efficiently culturing cells or tissues in a well dispersed state, and further, permitting cell image analysis of the cells or tissues.

Means of Solving the Problems

The present inventors have conducted intensive studies in an attempt to solve the aforementioned problems and found that cells and tissues can be dispersed well by using agar as a medium additive, and efficient culture can be performed both in a floating state and a sedimented state depending on the concentration of agar. Furthermore, they have found that cells and tissues can be analyzed quickly and conveniently by a cell imaging apparatus when they are cultured in a composition using the medium additive, which resulted in the completion of the present invention.

That is, the present invention provides the following.
[1] A medium additive comprising agar.
[2] The medium additive of [1], wherein the agar has a weight average molecular weight of 10,000-60,000.
[3] The medium additive of [1] or [2], which is a liquid.
[4] The medium additive of [3], wherein a content of the agar is 0.001 (w/v) %-5 (w/v) % relative to the total amount of the medium additive.
[5] A medium composition comprising agar.
[6] The medium composition of [5], wherein the agar has a weight average molecular weight of 10,000-60,000.
[7] A medium composition comprising the medium additive of any one of [1] to [4].
[8] The medium composition of any one of [5] to [7], wherein a content of the agar is not less than 0.005 (w/v) % and less than 2 (w/v) % relative to the total amount of the medium composition.

[9] The medium composition of any one of [5] to [8], having a viscosity at 37° C. of not more than 2.5 mPa·s when the agar content is 0.1 (w/v) %.
[10] The medium composition of any one of [5] to [9], which is for cell culture.
[11] The medium composition of [10], wherein the cell is an adherent cell or a floating cell.
[12] The medium composition of [11], wherein the adherent cell is adhered to a carrier surface or embedded in a carrier inside.
[13] The medium composition of [11], wherein the adherent cell is adhered to a microcarrier.
[14] The medium composition of [11], wherein the adherent cell forms a sphere.
[15] The medium composition of any one of [11] to [14], wherein the adherent cell is selected from the group consisting of a cancer cell, a hepatocyte and a cancer cell line.
[16] A cell or tissue culture comprising the medium composition of any one of [5] to [15] and cells or tissues.
[17] A method of culturing a cell or tissue, comprising cultivating the cell or tissue in a dispersed state in the medium composition of any one of [5] to [15].
[18] The method of [17], wherein the cell is an adherent cell or a floating cell.
[19] The method of [18], wherein the adherent cell is adhered to a carrier surface or embedded in a carrier inside.
[20] The method of [18], wherein the adherent cell is adhered to a microcarrier.
[21] The method of [18], wherein the adherent cell forms a sphere.
[22] The method of any one of [18] to [21], wherein the adherent cell is selected from the group consisting of a cancer cell, a hepatocyte and a cancer cell line.
[23] A method of screening for a pharmaceutical product candidate substance, comprising
(a) a step of cultivating a cell in the presence of a test substance and in the absence thereof in the medium composition of any one of [5] to [15], and
(b) a step of analyzing changes in the physiological function of the cell.
[24] The method of [23], further comprising (c) a step of selecting, as a pharmaceutical product candidate substance, a substance that suppresses or increases the physiological function of the cell than in the absence of the test substance.
[25] The method of [23] or [24], wherein (b) a step of analyzing changes in the physiological function of the cell is conducted by cell image analysis.
[26] The method of any one of [23] to [25], wherein a content of the agar is not less than 0.005 (w/v) % and less than 0.07 (w/v) % relative to the total amount of the medium composition.
[27] A method of screening for an anticancer agent candidate substance, comprising
(a) a step of culturing a cancer cell or a cancer cell line in the medium composition of any one of [5] to [15] in the presence and in the absence of a test substance, and
(b) a step of analyzing changes in the proliferation of the cancer cell or cancer cell line.
[28] The method of [27], further comprising (c) a step of selecting, as an anticancer agent candidate substance, a substance that suppresses proliferation of cancer cell or cancer cell line than in the absence of the test substance.
[29] The method of [27] or [28], wherein (b) a step of analyzing changes in the proliferation of the cancer cell or cancer cell line is conducted by cell image analysis.
[30] The method of any one of [27] to [29], wherein a content of the agar is not less than 0.005 (w/v) % and less than 0.07 (w/v) % relative to the total amount of the medium composition.
[31] A method of producing a sphere, comprising cultivating an adherent cell in the medium composition of any one of [5] to [10].

Effect of the Invention

Using the medium additive or medium composition of the present invention, cells or tissues are dispersed well, and can be efficiently cultured in any of a floating state and a sedimented state.

Particularly, using the medium additive or medium composition of the present invention, adherent cells adhered to a carrier surface or embedded in a carrier inside, or adherent cells forming a sphere can be cultured in a well-dispersed state without causing excess coagulation.

Furthermore, by culturing using the medium additive or medium composition of the present invention, the properties and function of the cells can be analyzed by cell image analysis, and a candidate substance for a pharmaceutical product such as an anticancer agent and the like can be preferably screened for.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Figure 1:
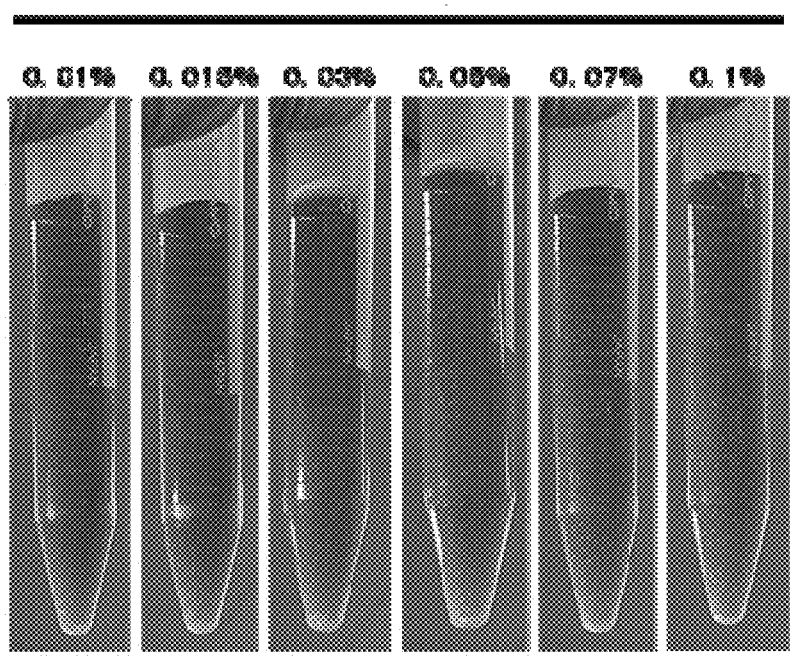
FIG. 1 shows the condition of polystyrene beads in a medium composition containing low-molecular agar in Analysis Example 1.

The present invention provides a medium additive containing agar.

In addition, the present invention also provides a medium composition containing agar.

Agar is composed of agarose and agaropectin in which agarose is partially sulfate esterified or substituted by methoxy group, pyruvic acid group, carboxyl group. The ratio of these constituent components is not limited, and agar may be constituted of agarose alone. In addition, low-melting-point agarose in which agarose is hydroxyethylated, low-melting-point agar prepared by selection of starting material seaweed or by hydroxyethylation and the like, rapid soluble agar showing high solubility in warm water and the like are also encompassed in the "agar" in the present invention.

In the present invention, powder, flake or solid agar produced industrially is preferably used since it has high purity and uniform quality. In addition, one generally used in the fields of pharmaceutical product, food and the like and having various properties and physical properties can be used, and low-molecular-weight agar having a weight average molecular weight of 10,000-60,000, low-strength agar having a weight average molecular weight of more than 60,000 and not more than about 100,000 and a low gel strength, high-molecular-weight agar having a weight average molecular weight of about 290,000 and the like can be used. As such agar, commercially available products can be utilized and, for example, "ultra agar Ena", "ultra agar AX-30", "ultra agar AX-100", "S-6", "S-7" and the like sold by Ina Food industry can be used.

In the present invention, it is preferable to use agar having a weight average molecular weight of 10,000-60,000, and having a lower molecular weight than general agar (hereinafter sometimes to be referred to as "low-molecular agar" in the present specification).

The average molecular weight of the low-molecular agar preferably used in the present invention is 10,000-60,000 as mentioned above, is more preferably 20,000-60,000, further preferably 30,000-60,000, further more preferably 40,000-60,000, still more preferably 43,000-60,000, particularly preferably 43,000-50,000.

When agar having a weight average molecular weight of less than 10,000 is used, a cell dispersing effect may be difficult to obtain. On the other hand, when agar having a weight average molecular weight of more than 60,000 is used, dispersion of cells or tissues in a medium may be non-uniform, and a sufficient proliferation promoting effect may not be obtained.

Furthermore, as the low-molecular agar to be used in the present invention, one having a narrow molecular weight distribution is preferable, and a molecular weight distribution (Mw/Mn), which is a value obtained by dividing weight average molecular weight (Mw) by number average molecular weight (Mn) of the agar, of preferably 1.1-8.0, more preferably 1.5-7.0, further preferably 2.0-6.0, still more preferably 2.5-5.5, particularly preferably 3.5-5.0.

The above-mentioned weight average molecular weight and number average molecular weight of agar can be measured by a gel penetration chromatography method by high performance liquid chromatography (HPLC).

Specifically, for example, the following measurement device, conditions and the like can be used for the measurement.

(1) measurement sample: Agar is dissolved in purified water to a concentration of, for example, about 0.15 (w/v) % ("(w/v) %" is "weight/% by volume", hereinafter the same) at 95° C.-97° C., cooled to 50° C., and used as a sample.

(2) measurement device: liquid chromatography LC-10AT VP, RID-10A etc. manufactured by Shimadzu Corporation (3) column: TOSOH TSK-GEL for HPLC, TSK-GEL GMPWXL etc. manufactured by Tosoh Corporation (4) solvent: 0.1 M aqueous sodium nitrate solution etc.

(5) detector: differential refractometer (6) measurement temperature: 50° C.

(7) standard substance: pullulan having known molecular weight (Shodex STANDARD P-82 etc.)

The low-molecular agar to be used in the present invention preferably has a gel strength, which is measured using 1.5 (w/v) % gel at 20° C., of not more than 25 $g/cm^2$, more preferably not more than 15 $g/cm^2$, further preferably not more than 12 $g/cm^2$.

The above-mentioned "gel strength" refers to a maximum load which a coagulated gel, obtained by standing a 1.5 (w/v) % aqueous solution of agar at 20° C. for 15 hr, can stand per 1 $cm^2$ surface for 20 seconds and can be measured, for example, according to the Regulation of Japan Industrial Standard (JIS) K 8263:1994 and using Nikkansui-type measuring apparatus.

Furthermore, the low-molecular agar to be used in the present invention preferably has a 1.5 (w/v) % gel extrusion load of 10 g-1,400 g, more preferably 10 g-1,000 g, further preferably 10 g-500 g, still more preferably 100 g-300 g.

The above-mentioned extrusion load can be determined by, for example, covering a hole (diameter 3 mm) at the center of the bottom of a cylindrical container (inner diameter 50 mm, height 110 mm, acrylic resin) attached to Texture Analyzer (manufactured by EKO Instruments Co., LTD.) with a tape, filling 1.5 (w/v) % aqueous solution (100 g) of agar, standing the mixture for 18 hr at 20° C. to allow for gellation, removing the bottom tape, applying pressure from the top of the gel with a plunger having a diameter of 49 mm (20° C., entrance speed 20 mm/min), and measuring the load when the gel breaks and flows out from the lower hole.

The above-mentioned low-molecular agar can be produced by a known method such as low-molecularization by a general acid treatment of agar, or an acid treatment during an extraction step from seaweed such as tengusa (*Gelidium amansii*), ogonori (*Gracilaria verrucosa*), obakusa (*Gelidiales Gelidiaceae*) and the like, or an acid treatment of agar after undergoing any of the aforementioned extraction step or filtration step, and the like. Products commercially available as low-molecular agar, for example, the above-mentioned "ultra agar Ena" (manufactured by Ina Food Industry) and the like can also be used.

Agar such as low-molecular agar and the like to be used in the present invention may be subjected to a sterilization treatment as necessary. The sterilization method is not particularly limited and, for example, radiation sterilization, ethylene oxide gas sterilization, autoclave sterilization and the like can be mentioned. These sterilization treatments can be applied whether agar is in a solid state or a solution state.

In the present invention, the above-mentioned agar may be directly used as a medium additive, or dissolved in a solvent such as water and the like, or mixed with components generally used for formulation such as excipient, binder and the like to give a solid medium additive such as powdery or granular form and the like, or a liquid medium additive such as aqueous solution and the like.

Alternatively, the above-mentioned agar may be mixed with a part of the following medium components such as carbohydrate, inorganic salt and the like to prepare a medium additive.

The medium additive of the present invention can be conveniently added to a medium used for culturing cells or tissues, and is preferably provided in a liquid form particularly from the aspect of miscibility with a liquid medium and the like.

A liquid medium additive is prepared as a solution by dissolving agar in a suitable solvent. Examples of the solvent usable in the present invention include, but are not limited to, polar solvents such as water; dimethyl sulfoxide (DMSO); lower alcohol such as methanol, ethanol, propanol, butanol and the like; polyvalent alcohol such as propylene glycol, butyleneglycol, glycerol and the like, and the like. A particularly preferable solvent is water, and the medium additive of the present invention is particularly preferably provided as an aqueous solution.

In the medium additive of the present invention, the content of agar is set such that the content of agar in the medium composition when added to the medium is a predetermined content to be described later.

The content of agar in a liquid medium additive such as aqueous solution and the like is preferably 0.001 (w/v) %-5 (w/v) %, more preferably 0.01 (w/v) %-2 (w/v) %, further preferably 0.1 (w/v) %-1 (w/v) %.

It is also possible to add other components that increase the effect of agar and can reduce its amount of use to the medium additive of the present invention. Examples of such component include uronic acid such as hexuronic acid (glucuronic acid, galacturonic acid etc.) and the like; polysaccharides such as guar gum, tamarind gum, alginic acid, alginic acid propyleneglycol ester, locust bean gum, gum arabic, tara gum, gellan gum, deacylated gellan gum, Rhamsan gum, diutan gum, xanthan gum, carrageenan, chitin, Fucoidan, pectin, pectin acid, pectinic acid, rhamnan sulfuric acid and the like and a derivative thereof; mucopolysaccharides such as hyaluronic acid, heparan sulfuric acid, heparin, keratan sulfate, chondroitin sulfate, dermatansulfuric acid and the like; cellulose derivatives such as methylcellulose, hydroxyethylcellulose, hydroxypropylcellulose, carboxymethylcellulose and the like; hydrophilic polymer such as carboxyvinyl polymer, acrylic acid.methacrylic acid alkyl copolymer and the like; salts thereof and the like. One or more kinds of the aforementioned components can be selected and used. The content of the aforementioned component in the medium additive of the present invention is preferably 0.001 (w/v) %-5 (w/v) %, more preferably 0.01 (w/v) %-2 (w/v) %, further preferably 0.1 (w/v) %-1 (w/v) %.

The medium additive of the present invention to be provided in the form of an aqueous solution is prepared by adding agar and other components as necessary to water, dissolving the mixture by heating to 90° C.-97° C., and preferably subjecting to a sterilization treatment.

The method for sterilization treatment is not particularly limited and, for example, autoclave sterilization at 121° C. for 20 min, radiation sterilization, ethylene oxide gas sterilization, filter filtration sterilization and the like can be mentioned.

When filter filtration sterilization (hereinafter sometimes to be referred to as filtration sterilization) is to be performed, the material of the filter part is not particularly limited and, for example, glass fiber, nylon, PES (polyethersulfone), hydrophilic PVDF (polyvinylidene fluoride), cellulose mixed ester, celluloseacetate, polytetrafluoroethylene and the like can be mentioned. While the size of the pore in the filter is not particularly limited as long as the medium additive of the present invention passes through and microorganism does not, it is preferably 0.1 μm to 10 μm, more preferably 0.1 μm to 1 μm, most preferably 0.1 μm to 0.5 μm. The temperature of the medium additive during filter filtration sterilization is preferably 30° C.-80° C., more preferably 40° C.-70° C., further preferably 50° C.-60° C.

The medium composition of the present invention contains the above-mentioned agar together with the medium components generally used for culturing cells or tissues.

The above-mentioned agar may be added as the above-mentioned medium additive of the present invention to medium components used generally.

Examples of the medium component generally used for culturing cells or tissues include hydrocarbonates such as glucose, fructose, sucrose, maltose and the like; amino acids such as asparagine, aspartic acid, glutamine, glutamic acid and the like; proteins or peptides such as albumin, transferrin and the like; serum; vitamins such as vitamin A, vitamin B group (thiamine, riboflavin, pyridoxine, cyanocobalamin, biotin, folic acid, pantothenic acid, nicotineamide etc.), vitamin C, vitamin E and the like; fatty acids or lipids such as oleic acid, arachidonic acid, linoleic acid, cholesterol and the like; inorganic salts such as potassium chloride, calcium chloride, magnesium sulfate, sodium chloride, sodium dihydrogen phosphate and the like; trace elements such as zinc, copper, selenium and the like; buffering reagents such as N,N-bis(2-hydroxyethyl)-2-aminoethanesulfonic acid (BES), 4-(2-hydroxyethyl)-1-piperazineethanesulfonic acid (HEPES), N-[tris(hydroxymethyl)methyl]glycine (Tricine) and the like; antibiotics such as amphotericin B, kanamycin, gentamicin, streptomycin, penicillin and the like; cell adhesion factors or intercellular matrices such as Type I collagen, Type II collagen, sodium chondroitin sulfate, fibronectin, laminin, poly-L-lysine, poly-D-lysine and the like; cytokines or growth factors such as interleukin, hepatocyte growth factor (HGF), transforming growth factor (TGF)-α, transforming growth factor (TGF)-β, vascular endothelium growth factor (VEGF) and the like; hormones such as dexamethasone, hydrocortisone, estradiol, progesterone, glucagon, insulin and the like, and the like. An appropriate component can be selected according to the cell or tissue to be cultured, and a medium composition can be prepared according to a known composition and used.

In the present invention, moreover, a medium widely used for culturing cells or tissues can also be used. Examples of such medium include a medium used for culturing animal cells such as hepatocytes, animal-derived tissues, and cancer cells, and a medium used for culturing plant cells or plant-derived tissues.

Examples of the culture medium for animal cell or animal-derived tissue include Dulbecco's Modified Eagle's Medium (DMEM), hamF12 medium (Ham's Nutrient Mixture F12), DMEM/F12 medium, McCoy's 5A medium, Eagle MEM medium (Eagle's Minimum Essential Medium; EMEM), αMEM medium (alpha Modified Eagle's Minimum Essential Medium; αMEM), MEM medium (Minimum Essential Medium), RPMI (Roswell Park Memorial Institute) 1640 medium, Iscove's Modified Dulbecco's Medium (IMDM), MCDB131 medium, William medium E, IPL41 medium, Fischer's medium, StemPro34 (manufactured by Invitrogen), X-VIVO 10 (manufactured by Cambrex Corporation), X-VIVO 15 (manufactured by Cambrex Corporation), HPGM (manufactured by Cambrex Corporation), StemSpan H3000 (manufactured by STEMCELL Technologies), StemSpanSFEM (manufactured by STEM- CELL Technologies), StemlineII (manufactured by Sigma Aldrich), QBSF-60 (manufactured by Qualitybiological), StemPro hESC SFM (manufactured by Invitrogen), Essential8 (registered trade mark) medium (manufactured by Gibco), mTeSR1 or 2 medium (manufactured by STEMCELL Technologies), ReproFF or ReproFF2 (manufactured by ReproCELL), PSGro hESC/iPSC medium (manufactured by System Biosciences), NutriStem (registered trade mark) medium (manufactured by Biological Industries), CSTI-7 medium (manufactured by Cell Science & Technology Institute, Inc.), MesenPRO RS medium (manufactured by Gibco), MF-Medium (registered trade mark) mesenchymal stem cell proliferation medium (manufactured by TOYOBO CO., LTD.), Sf-900II (manufactured by Invitrogen), OptiPro (manufactured by Invitrogen), and the like.

As the medium to be used for culturing cancer cells, the above-mentioned medium for culturing animal cells or animal-derived tissues and containing a cell adhesion factor can be used. Examples of the cell adhesion factor include Matrigel, collagen gel, gelatin, poly-L-lysine, poly-D-lysine, laminin, fibronectin and the like. One kind of these cell adhesion factors may be added alone, or not less than 2 kinds can be added in combination.

Examples of the medium to be used for culture of hepatocytes include, in addition to the above-mentioned media for culturing animal cells or animal-derived tissues, HepatoZYME-SFM (manufactured by Life Technologies), HCM (registered trade mark)-hepatocyte culture medium Bullet Kit (registered trade mark, manufactured by Lonza), HBM (registered trade mark)-hepatocyte basic medium (manufactured by Lonza), HMM (registered trade mark)-hepatocyte maintenance medium (manufactured by Lonza), modified Lanford's medium (manufactured by NISSUI PHARMACEUTICAL CO., LTD.), ISOM's medium, liver cell proliferation medium (manufactured by Takara Bio Inc.), hepatocyte maintenance medium (manufactured by Takara Bio Inc.), hepatocyte basic medium (manufactured by Takara Bio Inc.), activity maintenance super medium (manufactured by In Vitro ADMET Laboratories) and the like. These media can contain a cell adhesion factor such as Matrigel, collagen gel, gelatin, poly-L-lysine, poly-D-lysine, laminin, fibronectin and the like. One or more kinds of the aforementioned cell adhesion factors can be selected and added.

Examples of the medium for culturing plant cells or plant-derived tissues include basal media such as Murashige Skoog (MS) medium, Linsmaier Skoog (LS) medium, White medium, Gamborg's B5 medium, niche medium, hela medium, Morel medium and the like, and a medium obtained by adding auxins and, where necessary, a plant growth-regulating substance (plant hormone) such as cytokinins and the like at an appropriate concentration to a modified medium wherein those medium components are modified to an optimal concentration (e.g., ammonia nitrogen at a half concentration etc.). These media can be further supplemented, where necessary, with casein degrading enzyme, corn steep liquor, vitamins and the like. Examples of the auxins include, but are not limited to, 3-indoleacetic acid (IAA), 3-indolebutyric acid (IBA), 1-naphthaleneacetic acid (NAA), 2,4-dichlorophenoxyacetic acid (2,4-D) and the like. For example, auxins can be added to a medium at a concentration of about 0.1 ppm-about 10 ppm. Examples of the cytokines include, but are not limited to, kinetin, benzyladenine (BA), zeatin and the like. For example, cytokines can be added to a medium at a concentration of about 0.1 ppm-about 10 ppm.

In the present invention, an appropriate medium can be selected and used according to the kind of the cells or tissues to be cultured, the purpose of culture, and the like. The above-mentioned medium may be prepared based on the composition thereof, or commercially available products provided by each company can also be used.

The content of agar in the medium composition of the present invention is preferably not less than 0.005 (w/v) % and less than 2 (w/v) %, more preferably not less than 0.03 (w/v) % and less than 2 (w/v) %, further preferably 0.03 (w/v) %-1 (w/v) %, further more preferably 0.03 (w/v) %-0.1 (w/v) %, relative to the total amount of the medium composition.

When the content of agar in the medium composition is not less than 0.005 (w/v) %, cells, spheres formed from one cell, or tissues proliferate without forming excessively large aggregate, and cell proliferation promoting effect under low adhesion conditions is observed. In addition, a content of agar in the medium composition of not less than 0.03 (w/v) % is more preferable, since uniform dispersion of the cells or tissues can be achieved. On the other hand, when the content of agar in the medium composition is not less than 2 (w/v) %, handling may become difficult since gelation sometimes occurs at room temperature.

The content of agar in the medium composition of the present invention can be selected to achieve an appropriate concentration according to the kind of cells or tissues to be cultivated, the culture method, the purpose of culture, and the like, as described later.

In the present invention, the above-mentioned medium composition containing a low concentration of agar having a low molecular weight as compared to general agar is preferable, since it is a medium composition having low viscosity and easily handled even though it can be used for microcarrier culture and sphere culture.

In the present invention, the viscosity of a medium composition having an agar content of 0.1 (w/v) % is preferably not more than 3 mPa·S, more preferably not more than 2.5 mPa·S, further preferably not more than 2.1 mPa·S, when measured under the conditions described below at 37° C. with an E type viscometer. A medium composition with such low viscosity can be easily prepared using the above-mentioned low-molecular agar.

The medium composition of the present invention can be prepared according to a known method. For example, it can be prepared by adding medium components and agar to purified water to a predetermined concentration, dissolving the mixture by heating to 90° C.-97° C., and performing autoclave sterilization at 121° C. for 20 min.

In addition, it can also be prepared by adding agar to purified water to a concentration of 0.6 (w/v) %-2 (w/v) %, dissolving the mixture by heating to 90° C.-97° C., performing autoclave sterilization at 121° C. for 20 min, and mixing the prepared aqueous agar solution and a predetermined amount of an optional medium.

Furthermore, it can also be prepared by adding agar to purified water to a concentration of 0.01 (w/v) %-0.2 (w/v) %, dissolving the mixture by heating to 90° C.-97° C., performing autoclave sterilization at 121° C. for 20 min, and mixing the prepared aqueous agar solution and a predetermined amount of a medium containing components concentrated to not less than 2-fold.

The temperature of the optional medium when mixed with the aqueous agar solution is preferably 25° C.-80° C., more preferably 30° C.-50° C., further preferably 32° C.-37° C. The temperature of the aqueous agar solution at that time is preferably 30° C.-80° C., more preferably 40° C.-70° C., further preferably 50° C.-60° C.

Alternatively, it can be prepared by adding the above-mentioned medium additive and medium component of the present invention to purified water each to a predetermined concentration, dissolving the mixture by heating as mentioned above, and performing autoclave sterilization, or by adding the sterilization-treated medium additive of the present invention to a medium to a predetermined agar concentration.

The aqueous agar solution to be used for preparation of the medium composition of the present invention can be prepared similarly to the above-mentioned medium additive in the form of an aqueous solution, and can be sterilization-treated similarly.

The medium composition of the present invention can be preferably used for culturing cells or tissues.

The "cell" here is a most basic unit constituting animals and plants, which has, as its elements, cytoplasm and various organelles inside the cellular membrane. In this case, the nucleus encapsulating the DNA may or may not be contained intracellularly.

The animal-derived cells include reproductive cells such as spermatozoon, oocyte and the like, somatic cells constituting the living body, stem cells, progenitor cells, cancer cells, cells separated from the living body, which acquired immortalizing ability and are maintained stably in vitro (cell line), cells separated from the living body and applied with artificial genetic modification, cells separated from the living body wherein the nucleus is artificially exchanged, and the like.

Examples of the somatic cells constituting the living body include, but are not limited to, fibroblast, bone marrow cells, B lymphocytes, T lymphocytes, neutrophils, red blood cells, platelets, macrophages, monocytes, osteocytes, bone marrow cells, pericytes, dendritic cells, adipocytes, mesenchymal cells, epithelial cells, epidermal cells (e.g., keratinized cell (keratinocytes), cornified cell etc.), endothelial cells, vascular endothelial cells, hepatocytes, chondrocytes, cumulus cells, nerve cells, glial cells, oligodendrocytes (oligodendrocyte), microglial (microglia), astrocytes, heart cells, esophagus cells, myocytes (e.g., smooth muscle cells or skeletal muscle cells), pancreas beta cells, melanin cells, mononuclear cells and the like.

The somatic cells include cells collected from any tissue, for example, skin, kidney, spleen, adrenal gland, liver, lung, ovary, pancreas, uterus, stomach, colon, small intestine, large intestine, bladder, prostate, testis, thymus, muscle, connective tissue, bone, cartilage, blood vessel tissue, blood (including cord blood), bone marrow, heart, eye, brain, nerve tissue and the like.

Stem cells are cells concurrently having an ability to replicate itself, and an ability to differentiate into other plural lineages. Examples thereof include, but are not limited to, adult stem cells such as neural stem cells, hematopoietic stem cells, mesenchymal stem cells, liver stem cells, pancreas stem cells, muscle stem cells, germ stem cells, intestinal stem cells, hair follicle stem cells and the like, pluripotent stem cells such as embryonic stem cells (ES cell), embryonic carcinoma cell, embryonic germ stem cells, induced pluripotent stem cells (iPS cell) and the like, cancer stem cells and the like.

Progenitor cells are cells on the way to differentiate from the aforementioned stem cell into a particular somatic cell or reproductive cell, and include satellite cell, pancreatic progenitor cell, blood vessel progenitor cell, vascular endothelial progenitor cell, hematopoietic progenitor cell (cord blood-derived CD34 positive cell etc.).

Cancer cells are cells that are derived from a somatic cell and have acquired infinite proliferative capacity, and include cells of cancer tissues from gastric cancer, esophagus cancer, large intestine cancer, colorectal cancer, rectal cancer, pancreatic cancer, breast cancer, ovarian cancer, prostate cancer, flat epithelial cell cancer, basal cell carcinoma, glandular cancer, bone marrow cancer, kidney cell cancer, ureter cancer, liver cancer, cholangiocarcinoma, cervical cancer, uterine body cancer, testis cancer, small cell lung cancer, non-small cell lung cancer, urinary bladder cancer, epithelial cancer, craniopharyngioma, laryngeal cancer, cancer of the tongue, fiber sarcoma, mucosasarcoma, liposarcoma, chondrosarcoma, osteogenic sarcoma, chordoma, blood vessel sarcoma, lymphangiosarcoma, lymphangioendothelial sarcoma, synovial sarcoma, mesothelioma, Ewing's tumor, leiomyosarcoma, rhabdomyosarcoma, seminoma, Wilms' tumor, glioma, astrocytoma, bone marrow sarcoma, meningioma, melanoma, neuroblastoma, medulloblastoma, retina blastoma, malignant lymphoma, and blood derived from cancer patients and the like.

Examples of the cancer cell line include HBC-4, BSY-1, BSY-2, MCF-7, MCF-7/ADR RES, HS578T, MDA-MB-231, MDA-MB-435, MDA-N, BT-549, T47D as human breast cancer cell lines, HeLa, C-33A as human cervical carcinoama cell lines, A549, EKVX, HOP-62, HOP-92, NCI-H23, NCI-H226, NCI-H322M, NCI-H460, NCI-H522, DMS273, DMS114 as human lung cancer cell line, Caco-2, COLO-205, HCC-2998, HCT-15, HCT-116, HT-29, KM-12, SW-620, WiDr as human large intestine cancer cell line, DU-145, PC-3, LNCaP as human prostate cancer cell line, U251, SF-295, SF-539, SF-268, SNB-75, SNB-78, SNB-19 as human central nervous system cancer cell line, OVCAR-3, OVCAR-4, OVCAR-5, OVCAR-8, SK-OV-3, IGROV-1 as human ovarian cancer cell line, RXF-631L, ACHN, UO-31, SN-12C, A498, CAKI-1, RXF-393L, 786-0, TK-10 as human renal cancer cell line, MKN45, MKN28, St-4, MKN-1, MKN-7, MKN-74 as human gastric cancer cell line, LOX-IMVI, LOX, MALME-3M, SK-MEL-2, SK-MEL-5, SK-MEL-28, UACC-62, UACC-257, M14 as skin cancer cell line, CCRF-CRM, K562, MOLT-4, HL-60 TB, RPMI8226, SR, UT7/TPO, Jurkat as leukemia cell line, A431 as human epithelial like cancer cell line, A375 as human melanoma cell line, MNNG/HOS as human osteosarcoma cell line, MIAPaCa-2 as human pancreatic cancer cell line, Ns0, Ns1 as mouse myeloma cell line, PC12 as rat pheochromocytoma-derived cell line, and the like.

Examples of the normal cell-derived cell line include CHOK1 cell (ATCC CCL-61 (trade mark)), CHO-S cell, CHO-DG44 cell (Chinese hamster ovary-derived), HEK293 (human embryonic kidney cell-derived), MDCK (canine kidney renal tubule epithelial cell-derived), MDBK (bovine kidney-derived), BHK (Syrian hamster kidney-derived), AE-1 (mouse splenocyte-derived), NIH3T3 (mouse embryo fibroblast-derived), S2 (*Drosophila* embryo-derived), Sf9 (cabbage armyworm ovary cell-derived), Sf21 (cabbage armyworm ovary cell-derived), High Five (registered trade mark, *Trichoplusia ni* ovum cell-derived), Vero (African green monkey kidney epithelial cell-derived) and the like.

Examples of the hepatocytes include primary hepatocytes collected from liver tissue, hepatocyte strain established by passage culture under conditions optimized for in vitro culture, and hepatocytes differentiated and induced in vitro from cells derived from a tissue other than the liver, pluripotent stem cells such as iPS cells, ES cells and the like, mesenchymal stem cells, stem cells derived from peripheral blood, myeloid stem cells, adipose stem cells, liver stem cells, liver progenitor cells, and the like.

The liver tissue is a liver collected from human, rat, mouse, guinea pig, hamster, rabbit, swine, bovine, horse, dog, cat, monkey etc., which may be a normal liver or a cancerated liver.

While the primary hepatocytes can be separated and recovered from the above-mentioned liver tissues by a perfusion method using collagenase, it may be purchased from reagent companies such as Primarycell, Japan Becton Dickinson and Company, Takara Bio Inc., Hokkaido System Science Co., Ltd., Lonza Japan, Veritas Ltd., Life Technologies Japan Corporation and the like. The purchased hepatocytes may be in a frozen state or attached to a carrier such as collagen and the like.

Examples of the hepatocyte cell lines include, but are not limited to, HepG2, Hep3B, HepaRG (registered trade mark), JHH7, HLF, HLE, PLC/PRF/5, WRL68, HB611, SK-HEP-1, HuH-4, HuH-7 and the like.

The plant-derived cell also includes cells separated from each tissue of a plant body, as well as a protoplast obtained by artificially removing the cell wall from the cell.

The "tissue" in the present invention is a unit of a structure which is an assembly in a certain manner of cells having some kinds of different properties and functions, and examples of the animal tissue include epithelial tissue, connective tissue, muscular tissue, nerve tissue and the like. Examples of the plant tissue include meristem, epidermis tissue, assimilation tissue, mesophyll tissue, conductive tissue, mechanical tissue, parenchyma tissue, dedifferentiated cell cluster (callus) and the like.

The medium composition of the present invention is preferably used for culturing cells, and more preferably used for culturing animal-derived cells mentioned above.

As mentioned above, cells derived from animals are divided into floating cells and adherent cells according to the properties during growth and proliferation. Examples of floating cell include cells present in the blood such as neutrophils, eosinophils, lymphocytes, macrophages and the like, and examples of adherent cell include epithelial cells, endothelial cells, nerve cells, fibroblasts and the like. The medium composition of the present invention can be preferably used for both floating cells and adherent cells. Since many of the somatic cells constituting the living body and the cell lines derived from somatic cells or cancer cells are adherent cells, the medium composition of the present invention can be more preferably used for culturing adherent cells. The medium composition of the present invention can be particularly preferably used for culturing adherent cells in a state of being adhered to a carrier surface or embedded in a carrier inside or in a state of forming a sphere (cell aggregate).

In addition, the medium composition of the present invention is particularly preferably used for culturing cancer cells, hepatocytes and cancer cell lines.

Examples of the carrier capable of adhering adherent cells to a surface include microcarriers constituted of vinyl resin, urethane resin, epoxy resin, polystyrene, polymethylmethacrylate, polyester, polyamide, polyimide, silicon resin, phenol resin, melamine resin, urea resin, aniline resin, ionomer resin, polycarbonate, collagen, dextran, gelatin, cellulose, alginates, mixtures thereof, and the like, glass bead, ceramic bead, polystyrene bead, dextran bead and the like.

These carriers may be coated with a coating material that enhances cell adhesiveness or release of substance from the cells. Examples of such coating material include poly (monostearoylglycerides succinic acid), poly-D,L-lactid-co-glycolide, hyaluronate sodium, n-isopropylacrylamide, collagen I to XIX, fibronectin, vitronectin, laminin-1 to 12, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, sepharose, alginic acid gel, various hydrogels, and the like. Only one kind of these coating materials may be used alone, or two or more kinds thereof may be used in combination.

The carrier may also contain a magnetic material, for example, ferrite.

The diameter of the carrier is several tens of micrometers to several hundreds of micrometers, more preferably 100 µm to 200 µm, and its specific gravity is preferably close to 1, more preferably 0.9-1.2, particularly preferably about 1.0.

Examples of the carrier include, but are not limited to, Cytodex 1 (registered trade mark), Cytodex 3 (registered trade mark), Cytoline 1 (registered trade mark), Cytoline 2 (registered trade mark), Cytopore 1 (registered trade mark), Cytopore 2 (registered trade mark), (above, GE Healthcare Life Sciences), Biosilon (registered trade mark) (NUNC), Cultispher-G (registered trade mark), Cultispher-S (registered trade mark) (above, Thermo SCIENTIFIC), HILL-EXCT (registered trade mark), ProNectinF-COATED (registered trade mark), and HILLEXII (registered trade mark) (Solo Hill Engineering), GEM (registered trade mark) (Global Eukaryotic Microcarrier) and the like.

The carrier may be sterilized as necessary. The sterilization method is not particularly limited and, for example, radiation sterilization, ethylene oxide gas sterilization, autoclave sterilization, dry heat sterilization, and the like can be mentioned.

While the aforementioned cells can be adhered to the carrier by culturing adherent cells by using the carrier, the culturing method thereof is not particularly limited, and a culture method using a general flow layer-type culture vessel or filling layer-type culture vessel, and the like can be used.

As the carrier capable of embedding adherent cell in a carrier inside, a carrier formed from one or more kinds of polymer materials selected from hydrogels such as collagen, gelatin, alginates, chitosan, agarose, poly glycolic acid, polylactic acid, fibrin adhesive, polylactic acid-polyglycolic acid copolymer, proteoglycan, glycosaminoglycan, sponge such as polyurethane foam, temperature sensitive polymers (e.g., DseA-3D (registered trade mark), poly N-substituted acrylamide derivative, poly N-substituted methacrylamide derivative, and copolymers thereof, polyvinyl methylether, copolymer of propylene oxide and ethylene oxide, partially acetified poly(vinyl alcohol) etc.), polyacrylamide, poly (vinyl alcohol), methylcellulose, nitrocellulose, cellulose butyrate, polyethylene oxide, poly(2-hydroxyethylmethacrylate)/polycaprolactone and the like, and the like can be used.

The carrier can further contain a bioactive substance such as cell growth factor, differentiation inducing factor, cell adhesion factor, antibody, enzyme, cytokine, hormone, lectin, extracellular matrix and the like.

The method for embedding the adhesive cells in the above-mentioned carriers is not particularly limited and, for example, a method including aspirating a mixture of the above-mentioned cells and a polymer as a carrier formation material with a syringe and dropwise adding them to a medium from around 25G-19G injection needle, or dropwise adding to a medium using a micropipette, and the like can be used. The size of the bead-like carrier formed by such method is determined by the shape of the tip of a tool used for the dropwise addition of a mixture of the above-mentioned cell and the aforementioned polymers, which is preferably several tens of micrometers to several thousands of micrometers, more preferably 100 μm to 2000 μm. The number of cells that can be cultured by embedding in a bead-like carrier is not particularly limited, and can be freely selected according to the size of the bead-like carrier. For example, 5 million cells can be embedded in a bead-like carrier with a diameter of about 2000 μm. The embedded cells may be singly dispersed within the carrier or plural cells may assemble to form a sphere.

A method for forming an adherent cell aggregate (sphere) is not particularly limited, and can be appropriately selected by those of ordinary skill in the art from widely-used methods. Examples thereof include a method using a container having a cell non-adhesive surface, hanging drop method, gyratory culture method, Micromolding method, three-dimensional scaffold method, centrifugation method, a method using coagulation by an electric field or magnetic field and the like.

For example, using a method using a container having a cell non-adhesive surface, the object cells are cultured in a culture container applied with a surface treatment to inhibit cell adhesion, whereby a sphere can be formed. Such cell non-adhesive culture container is used, the object cells are first collected, a cell suspension thereof is prepared and plated in the culture container to perform culture. When culture is continued for about 1 week, the cells spontaneously form a sphere. As a cell non-adhesive surface used here, a surface of a culture container generally used such as schale and the like, which is coated with a substance inhibiting cell adhesion and the like can be used. Examples of the substance inhibiting cell adhesion include agarose, poly-HEMA (poly-(2-hydroxl-ethylmethacrylate), copolymer of 2-methacryloyloxyethylphosphoryl choline and other monomer (e.g., butylmethacrylate etc.), poly(2-methoxymethylacrylate), poly-N-isopropylacrylamide, mebiol gel (registered trade mark) and the like.

In addition, a medium for culturing for forming a sphere can also contain a component that promotes formation of a sphere or promotes maintenance thereof. Examples of the component having such effect include dimethyl sulfoxide, superoxide dismutase, caeruloplasmin, catalase, peroxidase, L-ascorbic acid, L-ascorbic acid phosphate, tocopherol, flavonoid, uric acid, bilirubin, selenium-containing compound, transferrin, unsaturated fatty acid, albumin, theophylline, forskolin, glucagon, dibutyryl cAMP and the like. As the selenium-containing compound, ROCK (Rho-associated coiled-coil-forming kinase) inhibitors such as sodium selenite, sodium selenate, dimethyl selenide, hydrogen selenide, Selenomethionine, Se-Methylselenocysteine (rac-(R*)-2-amino-3-(methylseleno)propanoic acid), Selenocystathionine, Selenocysteine, Selenohomocysteine, adenosine-5'-triphosphoric acid, Se-Adenosylselenomethionine (4-[5'-adenosyl(methyl)Selenonio]-2-aminobutyric acid), Y27632, Fasudil (HA1077), H-1152, Wf-536 and the like.

To obtain the object sphere having a uniform size, plural concaves having the same diameter as the object sphere can also be introduced onto a cell non-adhesive culture container to be used. When these concaves are in contact with each other or within the range of the diameter of the object sphere, and cells are plated, the plated cells do not form a sphere between concaves but certainly form a sphere with a size corresponding to the volume thereof in the concave, thus affording a sphere population having a uniform size. As the shape of the concave in this case is preferably a hemisphere or cone. Formation of such concave can be preferably performed by a micromolding method utilizing a template designed in advance.

Alternatively, a sphere can also be formed based on a support showing cell adhesiveness. Examples of such support include collagen, polyrotaxane, polylactic acid (PLA), polylactic acid glycolic acid (PLGA) copolymer, hydrogel and the like.

In addition, a sphere can also be formed by co-cultivating with a feeder cell. As a feeder cell to promote sphere formation, any adhesive cell can be used. Preferably, a feeder cell for each kind of cell is desirable. For example, when a sphere of cells derived from the liver or cartilage is formed, examples of the feeder cell include COS-1 cell and vascular endothelial cell as preferable cell types.

The culture container to be used for culturing sphere is not particularly limited as long as it generally permits animal cell culture. For example, flask, dish, schale, tissue culture dish, multidish, microplate, microwell plate, multiplate, multiwell plate, chamber slide, cell culture flask, spinner flask, tube, tray, culture bag, roller bottle, EZ SPHERE (manufactured by ASAHI GLASS CO., LTD.), Sumilon cell tight plate (manufactured by SUMITOMO BAKELITE) and the like can be mentioned.

The size (diameter) of the sphere used in the present invention varies depending on the cell type and culture period and is not particularly limited. When it has a spherical shape or ellipse spherical shape, it is 20 μm to 1,000 μm, preferably 40 μm to 500 μm, more preferably 50 μm to 300 μm, most preferably 80 μm to 200 μm.

In the state with formation of spheres by adherent cells, cell-cell interactions and cell structures close to those in the in vivo environment are reconstructed, the cell function can be maintained for a long term, and cell recovery is relatively easy. Therefore, cultured cells in the state with formation of spheres can be most preferably used for the analysis of physiological function of cells, screening for a pharmaceutical product candidate substance and the like, and the like. The medium composition of the present invention can be most preferably used for culturing such cells in the state with formation of spheres.

In the present invention, both a sphere formed by an assembly of a plurality of one kind of cells, and a sphere formed by an assembly of two or more kinds of cells are preferably used.

Furthermore, it is also possible to form a sphere from single cells by using the medium composition of the present invention. In this case, the concentration of agar in the medium composition is a concentration which can improve dispersion of cells and spheres without substantially increasing the viscosity of the medium composition and can prevent association of spheres. For example, it is preferably not less than 0.005 (w/v) % and less than 2 (w/v) %, more preferably not less than 0.03 (w/v) % and less than 2 (w/v) %, further preferably 0.03 (w/v) %-1 (w/v) %, further more preferably 0.03 (w/v) %-0.1 (w/v) %. Spheres are formed by dispersing the object cells in the medium composition of the present invention and culturing them by allowing to stand for 3 days-12 days. The spheres obtained here can be analyzed for the size, number, form, number of constituent cells and the like by using a microscope and a cell imaging apparatus. Such analysis is called sphere assay, spheroid colony assay, sphere formation assay, tumor formation assay or the like, and can be preferably used for classification and quantitative evaluation of cancer stem cells, neural stem cells, hematopoiesis precursor/stem cells and the like.

As mentioned below, using the medium composition of the present invention, a culture in which cells or tissues are dispersed well can be obtained without an operation of shaking during culture, stirring and the like.

According to the present invention, therefore, a culture maintained normally without impairing the function of the object cells or tissues can be obtained.

Using the medium composition of the present invention, moreover, proliferation of cells or tissues can be promoted well.

Particularly, when the above-mentioned low-molecular agar is used as the agar, a medium composition with low viscosity can be obtained, and the composition is preferable since it is superior in the dispersibility of cells or tissues and also superior in the proliferation promoting effect for cells or tissues.

The present invention also provides a method of culturing the above-mentioned cells or tissues in a dispersed state in the above-mentioned medium composition of the present invention.

In the culture method of the present invention, separately prepared cells or tissues are added to the medium composition of the present invention and mixed to be dispersed well. In this case, the mixing method is not particularly limited and, for example, manual mixing using pipetting and the like, mixing using instrument such as stirrer, vortex mixer, microplate mixer, shaking machine and the like can be mentioned. After mixing, the culture medium may be stood still, or the culture medium may be rotated, shaken or stirred as necessary. The rotating speed and frequency or shaking frequency can be appropriately set according to the kind of the cells or tissues to be cultured and the object of culture. To avoid damages on the function and the like of the cells or tissues, culturing in a stationary state is preferable.

When the medium composition needs to be exchanged during the standing culture period, the cells or tissues and the medium composition are separated by centrifugation or filtration treatment, and a new medium composition can be added of the cells or tissues. Alternatively, the cells or tissues are appropriately concentrated by centrifugation or filtration treatment, and a new medium composition can be added to the concentrated liquid.

The gravitational acceleration (G) of the above-mentioned centrifugation is, for example, 50G to 1,000G, more preferably 100G to 500G, and the size of the pore of the filter used for the filtration treatment is, for example, 10 μm to 100 μm. However, the gravitational acceleration and the size of the pore of the filter are not limited to these as long as the cells or tissues and the medium composition can be separated.

In addition, using magnetic fine particles coated, on the surface, with an antibody that specifically binds to the object cell, cultured cells or tissues can be separated by magnetic force. Examples of such magnetic fine particles include Dynabeads (manufactured by Veritas Ltd.), MACS microbead (manufactured by Miltenyi Biotec), BioMag (manufactured by Techno Chemicals Corporation), magnetic microsphere (manufactured by Polyscience, Inc.) and the like.

The temperature when cells or tissues are cultivated is generally 25° C. to 39° C., preferably 33° C. to 39° C., for animal cells. The $CO_2$ concentration is generally 4 (v/v) % ("(v/v) %" shows "volume/% by volume", hereinafter the same) to 10 (v/v) % in the culture atmosphere, and 4 (v/v) % to 6 (v/v) % is preferable. The culture period is generally 3 to 35 days, which may be appropriately set according to the object of the culture.

The culture temperature for plant cells is generally 20 to 30° C. and, when light is necessary, they can be cultured under illuminance conditions of illuminance 2000 lux-8000 lux. The culture period is generally 3 to 30 days, which may be appropriately set according to the object of the culture.

The cells or tissues cultured by the culture method of the present invention can be recovered by centrifugation or filtration using a filter, similarly to the above.

When the cells are adhered to the carrier, they can be recovered as they are by centrifugation at 50G-1,000G, preferably 100G-500G, or filtration using a filter having fine pores of about 10 μm-100 μm. In addition, cultured carriers can be recovered with a magnetic force by encapsulating a material having magnetism, such as ferrite, in the carrier.

Then, cultured cells can be detached and recovered from the recovered carrier by treatments with various chelating agents, heat treatment, enzyme treatment and the like.

When the cells are embedded in the carrier, they can also be recovered as they are by centrifugation at 50G-1,000G, preferably 100G-500G, or filtration using a filter having fine pores of about 10 μm-100 μm. In this case, a liquid medium contained in the medium composition used may be added and then centrifugation and filtration may be performed.

The cultured cells can be recovered by decomposing the carrier by treatments with various chelating agents, heat treatment, enzyme treatment and the like and dispersing the cells.

When the cells form a sphere, spheres cultured by the method of the present invention can be recovered by centrifugation at 50G-1,000G, preferably 100G-500G, or filtration using a filter having fine pores of about 10 μm-100 μm. In this case, a liquid medium contained in the medium composition used may be added and then centrifugation and filtration may be performed.

In addition, cultured spheres can be recovered by magnetic force by using magnetic fine particles coated, on the surface, with an antibody that specifically binds to the object cell, for example, the above-mentioned Dynabeads (manufactured by Veritas Ltd.), MACS microbead (manufactured by Miltenyi Biotec), BioMag (manufactured by Techno Chemicals Corporation), magnetic microsphere (manufactured by Polysciences Inc.) and the like.

The recovered sphere can be dispersed as a single cell by decomposing by treatments with various chelating agents, heat treatment, enzyme treatment and the like.

The above-mentioned cell recovery and exchange of the medium composition can also be achieved using a bioreactor and an automatic incubator capable of conducting under a mechanical control and under a closed environment.

Plant-derived cells or tissues can be statically cultured by the culture method of the present invention. In this case, callus, which is an undifferentiated plant cell aggregate, can be cultivated. Callus can be induced by a method known for each plant species to be used. For example, a surface of a part of a tissue of a differentiated plant body (e.g., root, stalk, leaf section, seed, growing point, embryo, pollen etc.) is sterilized, where necessary, with 70 (v/v) % alcohol, 1 (w/v) % aqueous sodium hypochlorite solution and the like, a tissue section with a suitable size (e.g., about 1 mm-about 5 mm square root section) is cut out with a knife and the like as necessary, the tissue section is plated on a callus induction medium sterilized in advance by an aseptic operation using a clean bench and the like, and aseptically cultivated under suitable conditions. The callus induced here may be subjected to liquid culture for mass proliferation, or may also be maintained as a seed strain by passaging in a passage medium. The passage culture may be performed using any of liquid medium and solid medium.

The amount of the plant cell aggregate inoculated when starting the standing culture using the medium composition of the present invention varies depending on the proliferation rate of the object cell, culture manner (batch culture, fed-batch culture, continuous culture etc.), culture period and the like. For example, when a plant cell aggregate such as callus and the like is to be cultivated, it is inoculated such that the wet weight of the cell aggregate relative to the medium composition of the present invention is 4 (w/v) %-8 (w/v))%, preferably 5 (w/v))%-7 (w/v) %. The particle size of the plant cell aggregate during culture is 1 mm to 40 mm, preferably 3 mm to 20 mm, more preferably 5 mm to 15 mm. As used herein, the "particle size" means a diameter when, for example, the plant cell aggregate has a spherical shape, a major axis when it has an ellipse spherical shape, and the maximum length possible when it has other shape.

The culture method of the present invention is preferably used for culturing animal-derived cells, and more preferably used for culturing adherent cells. Adherent cells are further preferably cultured in a state of being adhered to a carrier surface or embedded in a carrier inside, or in a state of forming a sphere, and particularly preferably used for culturing cancer cells, hepatocytes and cancer cell lines.

Using the culture method of the present invention, cells or tissues can be cultured well in a dispersed state even without an operation of shaking, stirring and the like.

According to the present invention, therefore, the object cells or tissues can be cultured while normally maintaining them without impairing the function thereof.

In addition, since proliferation of cells or tissues can be promoted by the culture method of the present invention, the cells or tissues can be efficiently cultured.

Furthermore, in the culture method of the present invention, the cells or tissues can be cultured in a floating state or precipitated state by adjusting the concentration of agar in the medium composition, and the culture state can be selected according to the kind of the cells or tissues to be cultured, the object of culture and the like.

The concentration of agar necessary for floating cells or tissues in the medium composition varies depending on the kind and state of the cells or tissues to be cultured, for example, a state of being adhered to a carrier or a state of forming a sphere and the like. It is preferably not less than 0.07 (w/v) %, more preferably not less than 0.1 (w/v) %, relative to the total amount of the medium composition.

As the agar, the above-mentioned low-molecular agar is preferably used, since it can lower the viscosity of the medium composition, has a superior proliferation promoting effect for cells or tissues, and affords good dispersion of cells or tissues.

The present invention further provides a method of screening for a pharmaceutical product candidate substance, comprising
(a) a step of cultivating a cell in the presence of a test substance and in the absence thereof in the above-mentioned medium composition of the present invention, and
(b) a step of analyzing changes in the physiological function of the cell.

The above-mentioned screening method of the present invention may further comprise (c) a step of selecting, as a pharmaceutical product candidate substance, a substance that suppresses or increases the physiological function of the cell than in the absence of the test substance.

The medium composition of the present invention and the culture method of the present invention using the composition can be particularly preferably used for culturing cancer cells, hepatocytes and cancer cell lines. Therefore, the above-mentioned screening method of the present invention can be particularly preferably applied to a method for screening for a pharmaceutical product candidate substance by using these cells, and can be preferably used for a screening method for an anticancer agent candidate substance against various carcinomas, or a method for evaluating efficacy or toxicity of a pharmaceutical product candidate substance in hepatocytes.

The method for screening for an anticancer candidate substance of the present invention includes (a) a step of culturing a cancer cell or a cancer cell line in the above-mentioned medium composition of the present invention in the presence and in the absence of a test substance, and (b) a step of analyzing changes in the proliferation of the cancer cell or cancer cell line. Furthermore, it can further comprise (c) a step of selecting, as a candidate substance for an anticancer agent, a substance that suppresses proliferation of cancer cell or cancer cell line as compared to that in the absence of the test substance.

The culture of cancer cell or cancer cell line in step (a) can be performed according to the above-mentioned culture method of the present invention.

The analysis of changes in the proliferation of the cancer cell or cancer cell line in step (b) can be performed by measuring the number of cells such as cancer cells and the like, evaluating toxicity to cells, and the like.

When the cell number is measured, colony formation method, crystal violet method, thymidine uptake method, Trypan Blue staining method, adenosine 3 phosphate (ATP) measurement method, 3-(4,5-dimethylthiazol-2-yl)-2,5-diphenyltetrazalium bromide (MTT) staining method, WST-1 (2-(4-Iodophenyl)-3-(4-nitrophenyl)-5-(2,4-disulfophenyl)-2H-tetrazolium, monosodium salt) staining method, WST-8 (2-(2-methoxy-4-nitrophenyl)-3-(4-nitrophenyl)-5-(2,4-disulfophenyl)-2H-tetrazolium, monosodium salt) staining method, flow cytometry, a method using a cell number automatic measuring apparatus, cell image analysis that detects and digitizes intracellular fluorescent signal and the like can be used. Among these, cell image analysis is most preferably used.

As a method for evaluating the cytotoxicity, lactic acid dehydrogenase (LDH) activity measurement method, Cyto-Tox-ONE (registered trade mark) method and the like can be used. Alternatively, cultured cell is stained with a specific antibody, cell surface differentiation marker is detected by Enzyme-Linked ImmunoSorbent Assay (ELISA) or flow cytometry, and the influence of the anticancer drug candidate substance on the proliferation and apoptosis of cancer cell can be observed. Furthermore, the gene that showed different expression due to the cancer candidate substance can be found by extracting the DNA (deoxyribonucleic acid) or RNA (ribonucleic acid) from the cultured cells and detecting by Southern Blotting, Northern Blotting, RT-PCR and the like.

In a method of evaluating the efficacy or toxicity of a pharmaceutical product candidate substance that acts on hepatocytes in the present invention, the changes in the physiological function of the hepatocytes in step (b) include proliferation or eradication of hepatocytes, increase or decrease in cytochrome P450 activity and the like.

The number of hepatocytes can be measured by a method similar to that for the above-mentioned cancer cells. Furthermore, the enzyme activity of cytochrome P450 can be measured by measuring the activity of the enzyme to convert the substrate structure by radioactive isotope method, high performance liquid chromatography method, luminescence method, color development method and the like.

As mentioned above, a culture in which dispersibility of the cells or tissues is improved can be obtained by performing cultivation using the medium composition and culture method of the present invention, and a culture, in which cells are dispersed well even when they are in a state of being adhered to a carrier surface or embedded in a carrier inside, or in a state of forming a sphere, can be obtained. Furthermore, the cells or tissues can be cultured in a floating state in a medium or in a precipitated state on the bottom of the culture container by adjusting the concentration of agar in the medium composition.

In the above-mentioned screening method of the present invention, to perform analysis of changes in proliferation of cancer cells and the like by the measurement of the number of cancer cells or cancer cell lines, evaluation of cytotoxicity and the like, and the like, and evaluation of changes in the physiological function of the hepatocytes by the measurement of the number of hepatocytes, measurement of cytochrome P450 activity and the like, it is preferable to obtain a culture in which cancer cells or cancer cell lines, hepatocytes and the like are precipitated on the bottom of the culture container without floating in the culture composition, but are in a well dispersed state.

To obtain a culture in such state, while the concentration of agar in the medium composition of the present invention varies depending on the kind and state of the cells or tissues to be cultured, for example, whether they are in a state of being adhered to a carrier or in a state of forming a sphere and the like, it is preferably not less than 0.005 (w/v) % and less than 0.07 (w/v) %, more preferably not less than 0.03 (w/v) % and less than 0.07 (w/v) %, further preferably 0.03 (w/v) %-0.05 (w/v) %.

When the concentration of agar in the medium of the present invention is not less than 0.03 (w/v) %, a culture in which dispersibility of the cells or tissues is further improved and the cells or tissues are uniformly dispersed can be obtained. Since a culture, in which cells or tissues are not suspended in the culture composition but precipitated on the bottom of the culture container, but they are in a state of uniform dispersion, can be directly analyzed by a cell imaging apparatus without repeating the operation to cause sedimentation of cells or tissues such as centrifugation and the like, or diluting the culture, the culture method and culture of the present invention can be preferably used for high content screening or high content analysis of a pharmaceutical product candidate substance by cell image analysis.

While an operation to cause sedimentation of a culture of cells or tissues by centrifugation and the like may be performed before analysis with a cell imaging apparatus, such operation is sufficient by performing once or so.

Examples of the cell imaging apparatus include "Opera Phenix" (registered trade mark) (manufactured by PerkinElmer), "Operetta" (registered trade mark) (manufactured by Perkin Elmer), "Cytel Cell Imaging System" (manufactured by GE^ Healthcare), "IN Cell Analyzer 2000 or 6000" (manufactured by GE Healthcare), "CellVoyager (registered trade mark) CV7000 (manufactured by Yokogawa Electric Corporation), "ArrayScan (registered trade mark) VTI HCS Reader" (manufactured by Thermo Fisher Scientific), "ArrayScan (registered trade mark) XTI HCA Reader" (manufactured by Thermo Fisher Scientific), "CellInsight (registered trade mark)" (manufactured by Thermo Fisher Scientific), "ImageXpress Micro" (manufactured by Molecular Devices) and the like. However, the cell imaging apparatus is not limited to these, and it suffices to examine the measurement target cells individually and in terms of plural parameters, in detail over time by utilizing fluorescence or bright field image data.

To obtain a culture, in which cells or tissues are not suspended in the culture composition but precipitated on the bottom of the culture container, but they are in a state of uniform dispersion, while the concentration of agar in the medium composition varies depending on the kind and state of the cells or tissues to be cultured, for example, whether they are in a state of being adhered to a carrier or in a state of forming a sphere and the like, it is preferably not less than 0.03 (w/v) % and less than 0.07 (w/v) %, more preferably 0.03 (w/v) %-0.05 (w/v) %, particularly preferably 0.03 (w/v) %.

Therefore, when cells or tissues are cultured for the purpose of screening for a pharmaceutical product candidate substance by cell image analysis, the concentration of agar in the medium composition of the present invention is preferably set to not less than 0.03 (w/v) % and less than 0.07 (w/v) %, more preferably 0.03 (w/v) %-0.05 (w/v) %, particularly preferably 0.03 (w/v) %.

As the agar in the present invention, the above-mentioned low-molecular agar is preferably used, since more uniform dispersion and better promotion of the proliferation of the cells or tissues can be achieved.

EXAMPLES

The present invention is explained in more detail in the following by concretely describing the Analysis Examples, Production Example and Experimental Examples of the medium composition of the present invention as Examples; however, the present invention is not limited thereto.

In the following Examples, the concentration (%) of $CO_2$ in the $CO_2$ incubator is shown by $CO_2$ (v/v) % in the atmosphere. "PBS" means phosphate buffered saline (manufactured by Sigma-Aldrich Japan), and "FBS" means fetal calf serum (manufactured by Biological Industries).

[Analysis Example 1] Floating Test of Polystyrene Beads in Medium Composition Containing Agar Preparation of Low-Molecular Agar-Containing Medium Composition, Medium Composition Containing Agar for General Use Low-molecular agar ("ultra agar Ena", manufactured by InaFood Industry) was suspended in pure water at 2.0 (w/v) %, and dissolved by heating with stirring at 90° C. The aqueous solution was stirred, and completely dissolved by autoclave sterilization at 121° C. for 20 min. The mixture was allowed to cool to room temperature, and the gelated aqueous low-molecular agar solution was redissolved by heating in a microwave oven. The aqueous solution (150 μL) was placed in a 15 mL centrifuge tube (manufactured by AS ONE Corporation), DMEM (Dulbecco's modified Eagle medium) (manufactured by Wako Pure Chemical Industries, Ltd.) (9.85 mL) heated to 37° C. was added, and the mixture was quickly stirred, whereby a medium composition having a final concentration of low-molecular agar of 0.03 (w/v) % was prepared. Similarly, medium compositions were prepared by adding the above-mentioned aqueous low-molecular agar solution to a final concentration of low-molecular agar of 0.07 (w/v) %, 0.10 (w/v) %. A medium composition containing agar for general use ("S-6", manufactured by InaFood Industry) was also prepared in the same manner.

The properties of the above-mentioned low-molecular agar and agar for general use are as described below.
(1) Weight Average Molecular Weight and Molecular Weight Distribution (Mw/Mn)

The weight average molecular weight and molecular weight distribution of the low-molecular agar measured using a 0.15 (w/v) % aqueous solution as a sample by a gel penetration chromatography-refractive index detector method by HPLC are 43,000 and 4.9.

On the other hand, the weight average molecular weight of the agar for general use is about 290,000.
(2) Strength of 1.5 (w/v) % Gel The gel strength of 1.5 (w/v) % gel measured according to the Regulation of JIS K 8263:1994 at 20° C. using Nikkansui-type measuring apparatus is 10 g/cm$^2$ for low-molecular agar and more than 630 g/cm$^2$ for agar for general use.
(3) 1.5 (w/v) % Gel Extrusion Load The 1.5 (w/v) % gel extrusion load measured by the method described above by a texture analyzer (manufactured by EKO Instruments Co., LTD.) (20° C., plunger diameter=49 mm, entrance speed=20 mm/min) is 170 g for low-molecular agar and not less than 2,000 g for agar for general use.

Floating Test of Polystyrene Beads in Low-Molecular Agar Containing Medium Composition and Medium Composition Containing Agar for General Use Polystyrene beads (manufactured by Polysciences, bead diameter=200 μm-300 μm, 600 μm) were suspended in each medium composition (10 mL) prepared above, incubated at 37° C. for 24 hr, and the dispersed state of polystyrene beads was visually observed. The results thereof are shown in Table 1 and Table 2.

Figure 2:
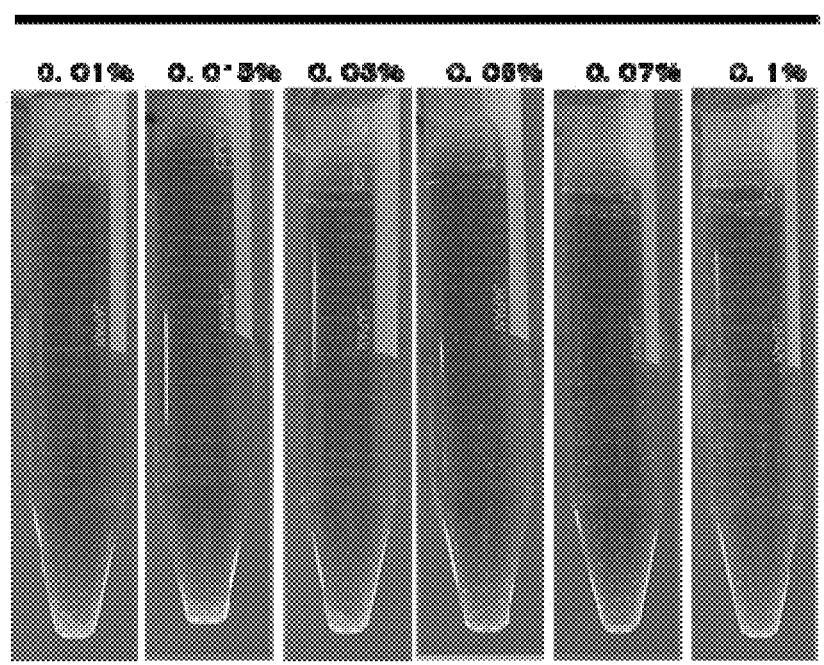
FIG. 2 shows polystyrene beads in a dispersed state in a medium composition containing agar for general use in Analysis Example 1.

In the same manner as in the above, medium compositions containing low-molecular agar and agar for general use each at concentrations of 0.01 (w/v) %, 0.015 (w/v) %, 0.05 (w/v) % were prepared, and the state of polystyrene beads dispersed in these medium compositions is shown in FIG. 1 and FIG. 2.

TABLE 1

| low-molecular agar concentration ((w/v)%) | state of medium | state of polystyrene beads |
| --- | --- | --- |
| 0.03 | liquid | precipitated |
| 0.07 | liquid | uniformly floating |
| 0.10 | liquid | uniformly floating |

TABLE 2

| agar for general use concentration ((w/v)%) | state of medium | state of polystyrene beads |
| --- | --- | --- |
| 0.03 | liquid | precipitated |
| 0.07 | liquid | floating but non-uniformly |
| 0.10 | liquid | floating but non-uniformly |

As shown in Tables 1, 2 and FIGS. 1, 2, it was clarified that polystyrene beads float in medium compositions containing low-molecular agar and agar for general use each at a concentration of not less than 0.07 (w/v) %.

In a medium composition containing agar for general use, dispersion of polystyrene beads was non-uniform, whereas uniform dispersion was observed in a medium composition containing low-molecular agar.

[Analysis Example 2] Measurement of Viscosity of Medium Composition Containing Agar and Cell Floating Test Preparation and Measurement of Viscosity of Low-Molecular Agar-Containing Medium Composition By a method similar to Analysis Example 1, medium compositions containing 0.03 (w/v) %, 0.05 (w/v) % and 0.10 (w/v) % of low-molecular agar in DMEM (manufactured by Wako Pure Chemical Industries, Ltd.) were prepared, and viscosity measurement was performed. The viscosity of the medium compositions was measured using an E type viscometer (manufactured by Toki Sangyo Co., Ltd., Viscometer TVE-22 L, standard roter 1° 34'×R24) under 37° C. condition at 100 rpm for 5 min.

The results thereof are shown in Table 3.

Cell Floating Test in Low-Molecular Agar-Containing Medium Composition

Human liver cancer cell line HepG2 (manufactured by DS PHARMA BIOMEDICAL CO., LTD.) was suspended in DMEM containing 10 (v/v) % FBS (manufactured by Wako Pure Chemical Industries, Ltd.) at 50,000 cells/mL, the suspension (10 mL) was seeded in EZ SPHERE (manufactured by Asahi Glass Co., Ltd.), and cultured in a $CO_2$ incubator (5% $CO_2$) for 2 days. A suspension (10 mL) of the spheres obtained here (diameter 100 μm-200 μm) was centrifuged (200G, 3 min) to form sedimentation of the spheres, and the supernatant was removed to prepare a sphere suspension (1.0 mL). Successively, the low-molecular agar-containing medium composition prepared above was placed in a 15 mL centrifuge tube (manufactured by AS ONE Corporation) by 10 mL, and HepG2 cell suspension (50 μL) was added. Cell aggregates were dispersed by tapping, incubated at 37° C., and the dispersed state of the cells was visually observed 7 days later. The results thereof are concurrently shown in Table 3. In addition, the state of the cells at the time of observation is shown in FIG. 3.

TABLE 3

| low-molecular agar concentration ((w/v)%) | viscosity (mPa·s) | state of HepG2 cells |
| --- | --- | --- |
| 0 | 1.126 | precipitated |
| 0.03 | 1.308 | precipitated |
| 0.07 | 1.624 | precipitated |
| 0.10 | 2.002 | floating |

Figure 3:
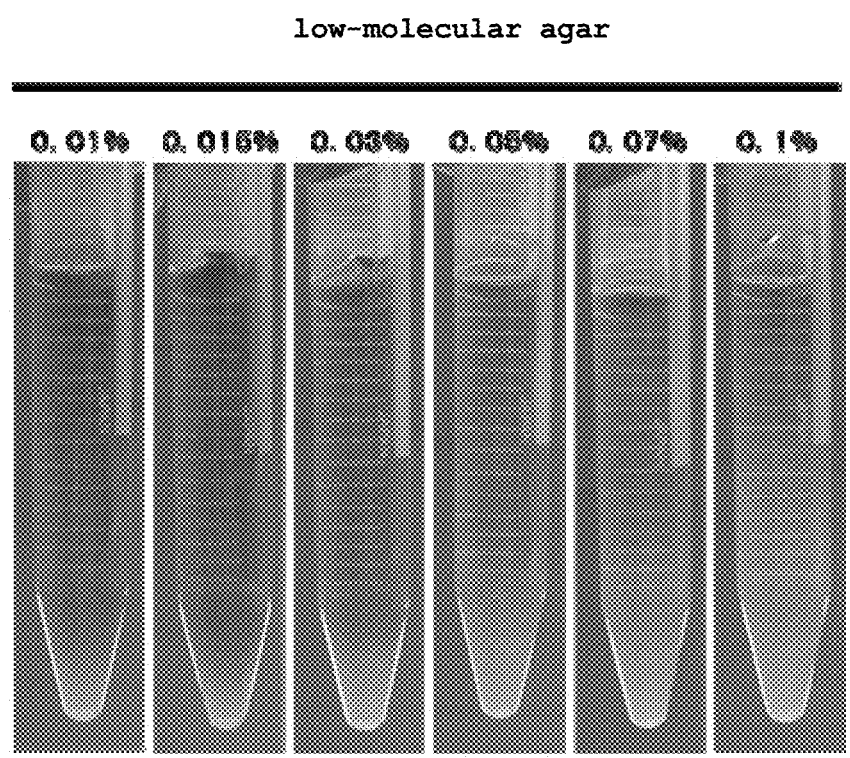
FIG. 3 shows the state of HepG2 cells after culturing for 7 days in a medium composition containing low-molecular agar in Analysis Example 2.

From the results shown in Table 3 and FIG. 3, it was found that the spheres of HepG2 cells can be floated by adding low-molecular agar to the medium composition at 0.1 (w/v) %, and the value of the viscosity of the medium composition is as low as 2.002 mPa·s.

[Analysis Example 3] Floating Test of Polystyrene Beads in Medium Composition Containing Agar Preparation of Low-Molecular Agar-Containing Medium Composition Low-molecular agar ("ultra agar Ena", manufactured by InaFood Industry) was suspended in pure water at 0.2 (w/v) %, and dissolved by heating with stirring at 90° C. The aqueous solution was stirred, and completely dissolved by autoclave sterilization at 121° C. for 20 min. Using a DMEM powder medium (manufactured by Sigma-Aldrich), 2-fold concentrated DMEM was prepared. The 2-fold concentrated DMEM was subjected to filtration sterilization by passing through a 0.22 µm filter (manufactured by Corning Incorporated). Equal amounts of the dissolved 0.2 (w/v) % aqueous low-molecular agar solution after autoclave sterilization and the aforementioned 2-fold concentrated DMEM medium heated to 37° C. were mixed and suspended to prepare DMEM containing 0.1 (w/v) % of low-molecular agar.

Floating Test of Polystyrene Beads in Low-Molecular Agar-Containing Medium Composition Polystyrene beads (manufactured by Polysciences, bead diameter 200 µm-300 µm, 600 µm) were suspended in the medium composition (10 mL) mentioned above, incubated at 37° C. for 24 hr, and the dispersed state of polystyrene beads was visually observed. The results thereof are shown in Table 4. In addition, the state of polystyrene beads during observation is shown in FIG. 4.

TABLE 4

| low-molecular agar concentration ((w/v)%) | state of medium | state of polystyrene beads |
|---|---|---|
| 0.1 | liquid | uniformly floating |

Figure 4:
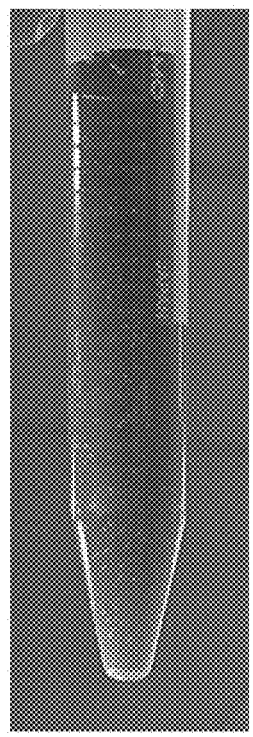
FIG. 4 shows the state of polystyrene beads in a medium composition containing low-molecular agar in Analysis Example 3.

As shown in Table 4 and FIG. 4, it was clarified that polystyrene beads float uniformly even when a medium composition containing 0.1 (w/v) % low-molecular agar was prepared by the above-mentioned preparation method.

[Production Example 1] Production of Medium Composition Containing Low-Molecular Agar Low-molecular agar ("ultra agar Ena", manufactured by Ina food Industry) was suspended in pure water at 0.06 (w/v) %, and dissolved by heating with stirring at 90° C. The aqueous solution was stirred, allowed to cool to an aqueous solution temperature of 42° C., and subjected to filtration sterilization with a filter with 0.22 µm diameter (manufactured by Corning Incorporated). In the same manner as in the method of Analysis Example 3, 2-fold concentrated DMEM was prepared. An equal amount of the 2-fold concentrated DMEM medium heated to 37° C. was added to the 0.06 (w/v) % aqueous low-molecular agar solution immediately after filtration sterilization, whereby a medium composition containing 0.03 (w/v) % of low-molecular agar was prepared.

Experimental Example

While the usefulness of the medium composition of the present invention in cell culture is concretely explained in the following Experimental Examples, the present invention is not limited thereto alone.

[Experimental Example 1] Cell Proliferation Test by Dispersing A549 Cells

By a method similar to the preparation method of medium composition in Analysis Example 1, medium compositions containing 10 (v/v) % FBS, and 0.005 (w/v) %, 0.03 (w/v) %, 0.07 (w/v) %, 0.10 (w/v) % of low-molecular agar or agar for general use in DMEM (manufactured by Wako Pure Chemical Industries, Ltd.) were prepared.

Then, adenocarcinomic human alveolar basal epithelial cell line A549 (manufactured by DS PHARMA BIOMEDICAL CO., LTD.) was seeded in each of the above-mentioned medium compositions containing low-molecular agar or agar for general use at 20,000 cells/mL, and dispensed to the wells of a 96 well flat bottom ultra-low attachment surface microplate (manufactured by Corning Incorporated, #3474) at 100 µL per 1 well. As the negative control, A549 cells were suspended in 10 (v/v) % FBS-containing DMEM free of low-molecular agar and agar for general use and the suspension was dispensed.

Successively, each microplate was cultured in a standing state in a $CO_2$ incubator (37° C., 5% $CO_2$) for 7 days. CellTiter-Glo Luminescent Cell Viability Assay (manufactured by Promega) (100 µL) was added to each cell culture medium after culturing for 2 days, 5 days, 7 days, the mixture was stood for 10 min at room temperature, and the amount of luminescence (Relative Light Unit; RLU) was measured by a microplate reader ("FlexStation 3", manufactured by Molecular Devices) and according to the protocol recommended by Promega. The amount of luminescence of each medium composition alone was subtracted, whereby the number of viable cells was measured.

Figure 5:
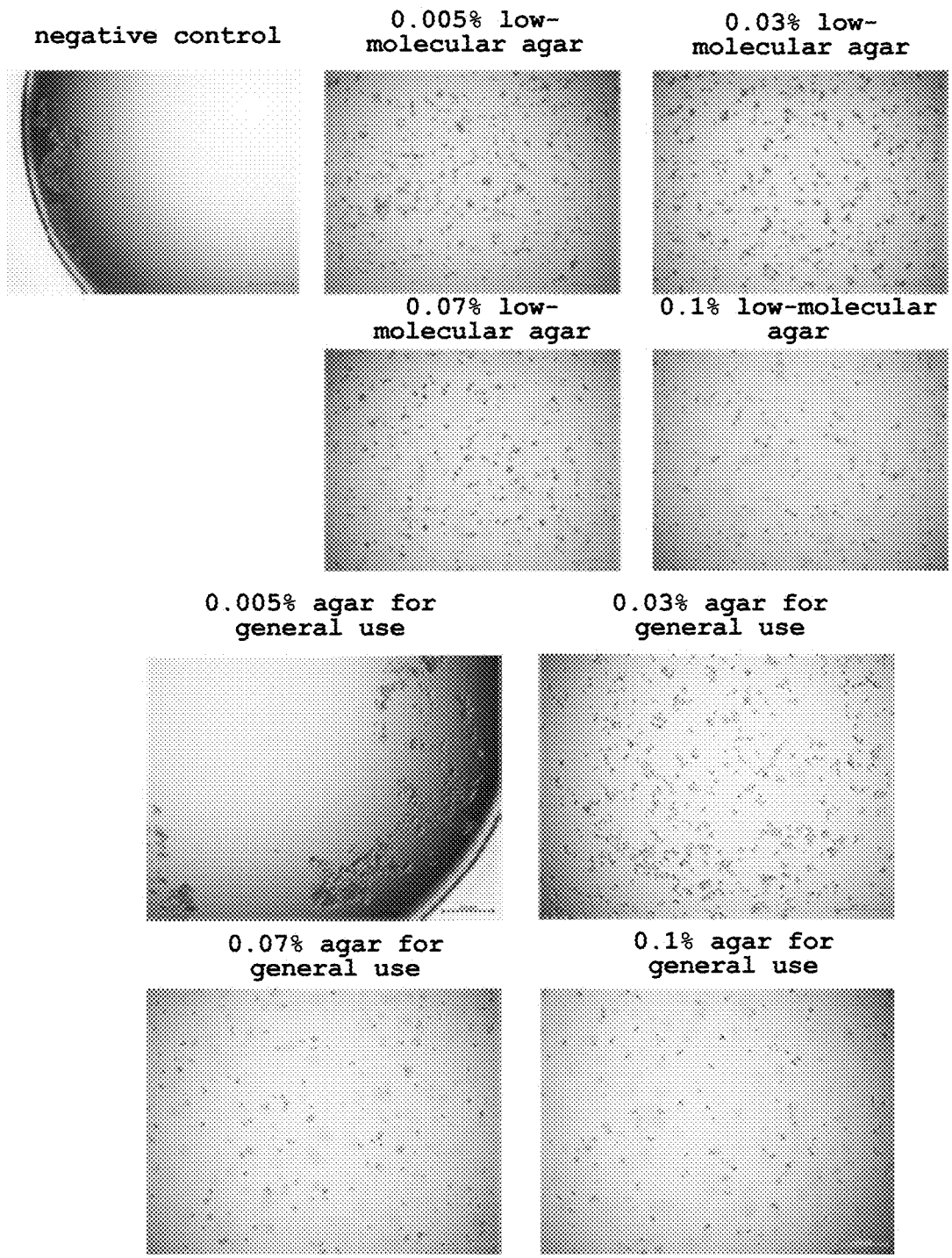
FIG. 5 shows the results of microscopic observation of a sphere of A549 cells after culturing for 7 days in Experimental Example 1.

The results of microscopic observation (instrument used: "inverted research microscope IX73" (manufactured by Olympus Corporation), magnification: ×40) of spheres of A549 cells after culturing for 7 days in each medium composition containing low-molecular agar or agar for general use are shown in FIG. 5. In addition, the state in the well and dispersibility of A549 cells after culturing for 7 days are shown in Table 5. Furthermore, the relative cell number when the amount of luminescence of the negative control is 1 was determined from the amount of luminescence (corresponding to the number of A549 cells) after stationary culture for 2 days, 5 days and 7 days in each medium composition containing low-molecular agar or agar for general use, and shown in Table 6.

TABLE 5

| sample | state of A549 cells | dispersibility of A549 cells |
|---|---|---|
| negative control | precipitated | non-uniform |
| low-molecular agar 0.005(w/v)% | precipitated | non-uniform |
| low-molecular agar 0.03(w/v)% | precipitated | uniform |
| low-molecular agar 0.07(w/v)% | floating | uniform |
| low-molecular agar 0.1(w/v)% | floating | uniform |
| agar for general use 0.005(w/v)% | floating | non-uniform and aggregated |
| agar for general use 0.03(w/v)% | floating | uniform |
| agar for general use 0.07(w/v)% | floating | uniform |
| agar for general use 0.1(w/v)% | floating | uniform |

TABLE 6

| | cell number | | |
|---|---|---|---|
| sample | 2 days | 5 days | 7 days |
| low-molecular agar 0.005(w/v)% | 1.267 | 2.277 | 2.525 |
| low-molecular agar 0.03(w/v)% | 1.176 | 2.263 | 2.534 |
| low-molecular agar 0.07(w/v)% | 1.209 | 2.529 | 2.863 |
| low-molecular agar 0.1(w/v)% | 1.172 | 2.470 | 2.924 |
| agar for general use 0.005(w/v)% | 1.037 | 1.921 | 1.876 |
| agar for general use 0.03(w/v)% | 0.861 | 1.815 | 1.772 |
| agar for general use 0.07(w/v)% | 1.044 | 2.192 | 2.239 |
| agar for general use 0.1(w/v)% | 0.872 | 1.894 | 2.022 |

From FIG. 5, it was observed that, in the negative control, spheres of the A549 cells were not dispersed in the medium but formed a large aggregate near the wall of the wells. In contrast, in a medium composition containing low-molecular agar or agar for general use, A549 cells form a sphere from one cell and coagulation was found in a medium composition having a concentration of the agar for general use of 0.005 (w/v) %. However, it was observed that association of the spheres did not occur, and the cells proliferated without forming an aggregate with an excess size.

From Table 5, it was shown that, in a medium composition containing not less than 0.03 (w/v) % of low-molecular agar or agar for general use, the dispersibility of the spheres of A549 cells was further improved, and the cells were cultured in a state of uniform dispersion. In a medium composition containing 0.005 (w/v) % or 0.03 (w/v) % of low-molecular agar or agar for general use, spheres of A549 cells were found to proliferate in a precipitated state on the bottom of the well. In a medium composition having a concentration of low-molecular agar or agar for general use of 0.03 (w/v) %, culturing in a uniformly dispersed state without floating in the medium was possible.

As shown in FIG. 5 and Table 5, it was found that spheres of A549 cells are cultured in a better dispersed state in a medium composition containing low-molecular agar as compared to a medium composition containing agar for general use.

From Table 6, moreover, promotion of cell proliferation was found in the medium compositions containing agar for general use and low-molecular agar as compared to a medium without addition of agar for general use or low-molecular agar as a negative control. In this case, it was found that cell proliferation is promoted more in a medium composition containing low-molecular agar as compared to the use of a medium composition containing the same concentration of agar for general use.

[Experimental Example 2] Cell Proliferation Test by Dispersing HepG2 Cells

By a method similar to the preparation method of medium composition in Analysis Example 1, a medium composition containing 10 (v/v) % FBS, and 0.03 (w/v) % of low-molecular agar or agar for general use in DMEM (manufactured by Wako Pure Chemical Industries, Ltd.) was prepared.

Then, human liver cancer cell line HepG2 (manufactured by DS PHARMA BIOMEDICAL CO., LTD.) was seeded in the above-mentioned medium composition containing low-molecular agar at 20,000 cells/mL, and dispensed to the wells of a 96 well flat bottom ultra-low attachment surface microplate (manufactured by Corning Incorporated, #3474) at 100 μL per 1 well. As the negative control, HepG2 cells were suspended in 10 (v/v) % FBS-containing DMEM and the suspension was dispensed.

Successively, the microplate was cultured in a standing state in a $CO_2$ incubator (37° C., 5% $CO_2$) for 7 days. CellTiter-Glo Luminescent Cell Viability Assay (manufactured by Promega) (100 μL) was added to each cell culture medium after culturing for 2 days, 5 days, 7 days, the mixture was stood for 10 min at room temperature, and the amount of luminescence was measured by a microplate reader ("SPECTRA MAX 190", manufactured by Molecular Devices) and according to the protocol recommended by Promega. The amount of luminescence of medium alone was subtracted, whereby the number of viable cells was measured.

Figure 6:
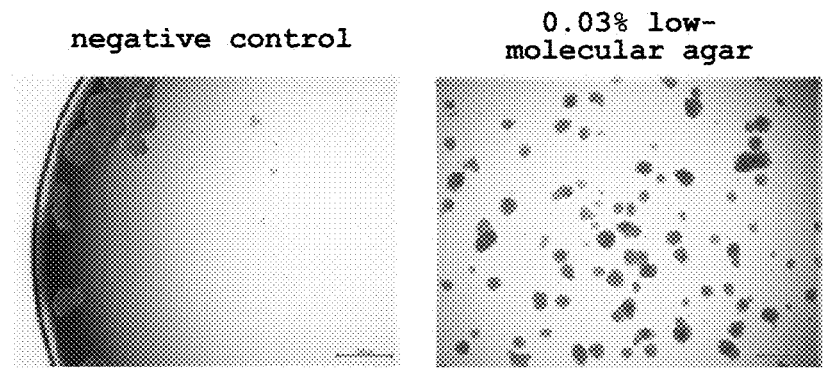
FIG. 6 shows the results of microscopic observation of a sphere of HepG2 cells after culturing for 7 days in Experimental Example 2.

The results of microscopic observation (instrument used: "inverted research microscope IX73" (manufactured by Olympus Corporation), magnification: ×40) of spheres of HepG2 cells after culturing for 7 days are shown in FIG. 6. In addition, the state in the well and dispersibility of HepG2 cells after culturing for 7 days are shown in Table 7. Furthermore, the relative cell number when the amount of luminescence of the negative control is 1 was determined from the amount of luminescence (corresponding to the number of HepG2 cells) after stationary culture for 2 days, 5 days and 7 days, and shown in Table 8.

TABLE 7

| sample | state of HepG2 cells | dispersibility of HepG2 cells |
|---|---|---|
| negative control | precipitated | non-uniform |
| low-molecular agar 0.03(w/v)% | precipitated | uniform |

TABLE 8

| | cell number | | |
|---|---|---|---|
| sample | 2 days | 5 days | 7 days |
| low-molecular agar 0.03(w/v)% | 0.984 | 1.316 | 2.044 |

As shown in FIG. 6, since HepG2 cells form a sphere from one cell and association of the spheres does not occur in the medium composition of the present invention containing low-molecular agar, the spheres were cultured in a state of uniform dispersion, without coagulating excessively largely. On the other hand, in the negative control, coagulation of the spheres of the HepG2 cells was observed near the wall of the wells.

As shown in Table 7, moreover, in the medium composition of the present invention containing low-molecular agar, spheres of HepG2 cells were precipitated on the bottom surface of the well but cultured in a uniformly dispersed state. Furthermore, from Table 8, promotion of the proliferation of HepG2 cells was observed in the medium composition of the present invention containing low-molecular agar as compared to a medium without addition of low-molecular agar as a negative control.

[Experimental Example 3] Cell Proliferation Comparison Test of Methylcellulose or Deacylated Gellan Gum-Containing Medium Compositions Preparation of Low-Molecular Agar-Containing Medium Composition and Deacylated Gellan Gum-Containing Medium Composition By a method similar to the preparation method of the medium composition of Analysis Example 1, medium compositions containing 10 (v/v) % FBS and 0.005 (w/v) %, 0.03 (w/v) %, 0.05 (w/v) %, 0.10 (w/v) % of low-molecular agar in DMEM (manufactured by Wako Pure Chemical Industries, Ltd.) were prepared. In addition, similar to the aqueous low-molecular agar solution, an aqueous solution containing 0.3 (w/v) % of deacylated gellan gum (KELCOGEL CG-LA, manufactured by Sansho Co., Ltd.) was prepared. Using the aqueous solution, a medium composition containing 10 (v/v) % FBS and 0.015 (w/v) % of deacylated gellan gum in DMEM (manufactured by Wako Pure Chemical Industries, Ltd.) was prepared.

Preparation of Methylcellulose-Containing Medium Composition

Methylcellulose (M0387, manufactured by Sigma-Aldrich) was suspended in pure water at 2.6 (w/v) %, and the suspension was subjected to autoclave sterilization at 121° C. for 20 min. The suspension was allowed to cool to room temperature, and stood at 4° C. overnight to give uniform methylcellulose. An equal amount of the 2-fold concentrated DMEM medium (Wako Pure Chemical Industries, Ltd.) containing 20 (v/v) % FBS was added to the 2.6 (w/v) % aqueous methylcellulose solution, whereby a medium composition containing 1.3 (w/v) % of methylcellulose was prepared. The medium was diluted with DMEM containing 10 (v/v) % FBS to prepare medium compositions containing 0.1 (w/v) %, 0.3 (w/v) %, 0.6 (w/v) % of methylcellulose.

Cell Proliferation Test when A549 Cells are Dispersed

Adenocarcinomic human alveolar basal epithelial cell line A549 (manufactured by DS PHARMA BIOMEDICAL CO., LTD.) was seeded in each of the above-mentioned medium compositions at 20,000 cells/mL, and dispensed to the wells of a 96 well flat bottom ultra-low attachment surface microplate (manufactured by Corning Incorporated, #3474) at 100 µL per 1 well. As the negative control, A549 cells were suspended in 10 (v/v) % FBS-containing DMEM and the suspension was dispensed.

Successively, the plate was cultured in a standing state in a $CO_2$ incubator (37° C., 5% $CO_2$) for 7 days. CellTiter-Glo Luminescent Cell Viability Assay (manufactured by Promega) (100 µL) was added to each cell culture medium after culturing for 2 days, 5 days and 7 days, the mixture was stood for 10 min at room temperature, and the amount of luminescence was measured by a microplate reader ("FlexStation 3", manufactured by Molecular Devices) and according to the protocol recommended by Promega. The amount of luminescence of each medium alone was subtracted, whereby the number of viable cells was measured.

Figure 7:
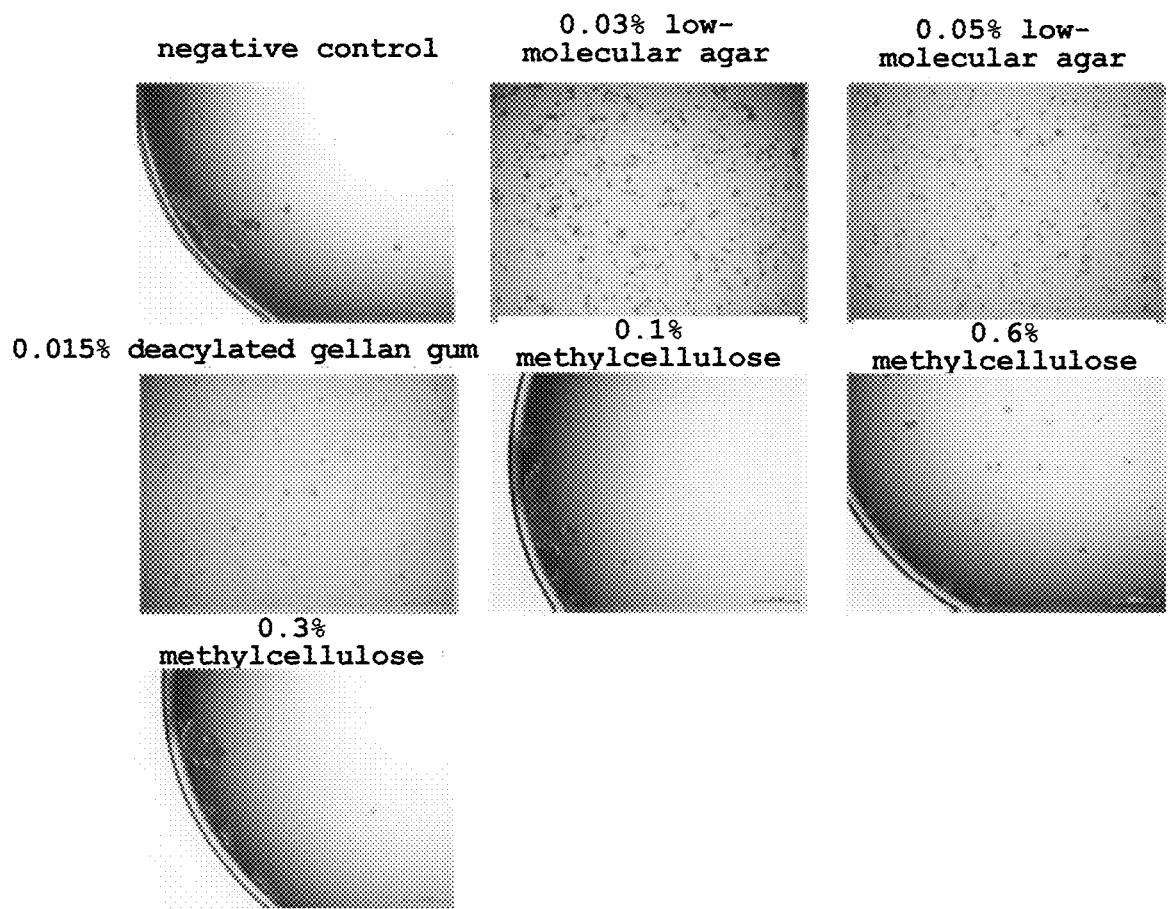
FIG. 7 shows the results of microscopic observation of a sphere of A549 cells after culturing for 7 days in Experimental Example 3.

The results of microscopic observation (instrument used: "inverted research microscope IX73" (manufactured by Olympus Corporation), magnification: ×40) of spheres of A549 cells after culturing for 7 days are shown in FIG. 7. In addition, the state in the well and dispersibility of A549 cells after culturing for 7 days are shown in Table 9. Furthermore, the relative cell number when the amount of luminescence of the negative control is 1 was determined from the amount of luminescence (corresponding to the number of A549 cells) after stationary culture for 2 days, 5 days and 7 days, and shown in Table 10.

TABLE 9

| sample | state of A549 cells | dispersibility of A549 cells |
| --- | --- | --- |
| negative control | precipitated | non-uniform |
| low-molecular agar 0.03(w/v)% | precipitated | uniform |
| low-molecular agar 0.05(w/v)% | floating | uniform |
| deacylated gellan gum 0.015(w/v)% | floating | uniform |
| methylcellulose 0.1(w/v)% | precipitated | non-uniform |
| methylcellulose 0.3(w/v)% | precipitated | non-uniform |
| methylcellulose 0.6(w/v)% | precipitated | non-uniform |

TABLE 10

| | cell number | | |
| --- | --- | --- | --- |
| sample | 2 days | 5 days | 7 days |
| low-molecular agar 0.03(w/v)% | 1.079 | 1.886 | 2.286 |
| low-molecular agar 0.05(w/v)% | 1.071 | 1.888 | 2.237 |
| deacylated gellan gum 0.015(w/v)% | 0.987 | 1.814 | 2.381 |
| methylcellulose 0.1(w/v)% | 0.941 | 0.793 | 0.743 |
| methylcellulose 0.3(w/v)% | 0.971 | 0.828 | 0.784 |
| methylcellulose 0.6(w/v)% | 1.043 | 1.005 | 1.011 |

As shown in FIG. 7 and Tables 9, 10, spheres of A549 cells proliferated well in a state of uniform dispersion in the medium composition of the present invention containing low-molecular agar, and the medium composition containing deacylated gellan gum, whereas spheres of A549 cells were non-uniformly dispersed, coagulation was observed, and a proliferation promoting effect was not found in the medium composition containing methylcellulose.

[Experimental Example 4] Cell Proliferation Test by Dispersing SKOV3 Cells

By a method similar to the preparation method of medium composition in Analysis Example 1, a medium composition containing 10 (v/v) % FBS, and 0.03 (w/v) % of low-molecular agar in DMEM (manufactured by Wako Pure Chemical Industries, Ltd.) was prepared.

Then, human ovarian cancer cell line SKOV3 (manufactured by DS PHARMA BIOMEDICAL CO., LTD.) was suspended in the above-mentioned medium composition containing low-molecular agar at 37,000 cells/mL, and dispensed to the wells of a 96 well flat plane ultra-low attachment surface microplate (manufactured by Corning Incorporated, #3474) at 135 µL per 1 well. The plate was stood in a $CO_2$ incubator (37° C., 5% $CO_2$), and a growth factor was added the next day. A similar operation was performed with 10 (v/v) % FBS-containing DMEM free of low-molecular agar. As a growth factor, human heparin bindability epithelial cell growth factor (hHB-EGF) (manufactured by PeproTech, Inc.) at a final concentration of 30 ng/mL or 100 ng/mL, human epithelial cell growth factor (hEGF) (manufactured by PeproTech, Inc.) and human transforming growth factor α (hTGFα) (manufactured by PeproTech, Inc.) each at a final concentration of 1 ng/mL, 3 ng/mL or 10 ng/mL were added by 15 µL per 1 well.

Successively, the plate was cultured in a standing state in a $CO_2$ incubator (37° C., 5% $CO_2$) for 10 days. As a negative control, DMEM in an amount equal to that of a growth factor was added. CellTiter-Glo Luminescent Cell Viability Assay (manufactured by Promega) (100 µL) was added to the cell culture medium after culturing for 10 days, stood for 10 min at room temperature, and the amount of luminescence was measured by a microplate reader ("FlexStation 3", manufactured by Molecular Devices) and according to the protocol recommended by Promega. The amount of luminescence of the medium composition alone was subtracted, whereby the number of viable cells was measured.

The relative cell number when the amount of luminescence of the negative control is 1 was determined from the amount of luminescence (corresponding to the number of SKOV3 cells) after culturing for 10 days after the addition of the growth factor, and shown in Table 11.

TABLE 11

| cell growth factor | low-molecular agar concentration ((w/v)%) | |
|---|---|---|
| | 0 | 0.03 |
| hHB-EGF 30 ng/mL | 1.358 | 1.774 |
| hHB-EGF 100 ng/mL | 1.451 | 1.748 |
| hEGF 1 ng/mL | 1.380 | 1.413 |
| hEGF 3 ng/mL | 1.392 | 1.745 |
| hEGF 10 ng/mL | 1.678 | 1.984 |
| hTGFα 1 ng/mL | 1.448 | 1.371 |
| hTGFα 3 ng/mL | 1.445 | 1.916 |
| hTGFα 10 ng/mL | 1.512 | 2.167 |

As shown in Table 11, as compared to the medium composition free of low-molecular agar, the medium composition of the present invention containing 0.03 (w/v) % of low-molecular agar showed growth factor concentration-dependent promotion of the proliferation of SKOV3 cells.

[Experimental Example 5] High Content Analysis of Anti-Cancer Agent Using Medium Composition Containing Low-Molecular Agar By a method similar to the preparation method of medium composition in Analysis Example 1, a medium composition containing 10 (v/v) % FBS, and 0.03 (w/v) % of low-molecular agar or agar for general use in DMEM (manufactured by Wako Pure Chemical Industries, Ltd.) was prepared. Paclitaxel (manufactured by Wako Pure Chemical Industries, Ltd.) was further added to a final concentration of 0.001 µM, 0.01 µM or 0.1 µM. Successively, adenocarcinomic human alveolar basal epithelial cell line A549 (manufactured by DS PHARMA BIOMEDICAL CO., LTD.) was seeded in the above-mentioned medium composition containing low-molecular agar at 5,000 cells/mL, and dispensed to the wells of a 96 well flat bottom ultra-low attachment surface microplate (manufactured by Corning Incorporated, #3474) at 100 µL per 1 well. Successively, the plate was cultured in a standing state in a $CO_2$ incubator (37° C., 5% $CO_2$) for 10 days.

Then, a solution of 200 mg/mL of Hoechst 33342 (manufactured by Invitrogen) in DMEM (phenol red, L-glutamine free) (manufactured by Wako Pure Chemical Industries, Ltd.) was prepared, and added, at 10 µL per 1 well, to the above-mentioned culture after static culture for 10 days, and the mixture was stood in a $CO_2$ incubator (37° C., 5% $CO_2$) for 45 min. Successively, a solution of 20 µg/mL Propidium Iodide (manufactured by BIOMOL) in DMEM (phenol red, L-glutamine free) (manufactured by Wako Pure Chemical Industries, Ltd.) was prepared and added at 10 µL per 1 well. The plate was centrifuged at 1,500 rpm for 10 min, and high content analysis was performed by cell image analysis using a cell imaging apparatus ("ArrayScan VTI HCS Reader", manufactured by Thermo Fisher Scientific). At that time, observation was performed with 10 fields of view per well using a ×4 objective lens, cell outline and cell nucleus were detected from Hoechst33342 fluorescence image, and dead cells were detected from propidium iodide fluorescence image. In addition, 50% inhibitory concentration (nM) of paclitaxel by high content analysis was calculated with the number of constituent cells when the anticancer agent was added at the maximum concentration as 100% inhibition rate of sphere formation.

As a negative control, a medium composition containing 10 (v/v) % FBS alone in DMEM (manufactured by Wako Pure Chemical Industries, Ltd.) was prepared. As a comparison control, in the same manner as in Experimental Example 3, a medium composition containing 10 (v/v) % FBS and 0.015 (w/v) % of deacylated gellan gum in DMEM (manufactured by Wako Pure Chemical Industries, Ltd.) was prepared. Paclitaxel was also added at the above-mentioned concentration to the negative control and comparison control medium compositions, A549 cells were suspended therein and the suspensions were dispensed. Successively, the plate was cultured in a standing state in a $CO_2$ incubator (37° C., 5% $CO_2$) for 10 days.

CellTiter-Glo Luminescent Cell Viability Assay (manufactured by Promega) (100 µL) was added to each cell culture medium of the negative control and comparison control, the mixture was stood for 10 min at room temperature, and the amount of luminescence was measured by a microplate reader ("FlexStation 3", manufactured by Molecular Devices) and according to the protocol recommended by Promega. The amount of luminescence of the medium alone was subtracted, whereby the number of viable cells was measured. In addition, 50% inhibitory concentration (nM) of paclitaxel by the amount of luminescence was calculated with the number of viable cells when paclitaxel was not added as 0% inhibition rate.

Figure 8:
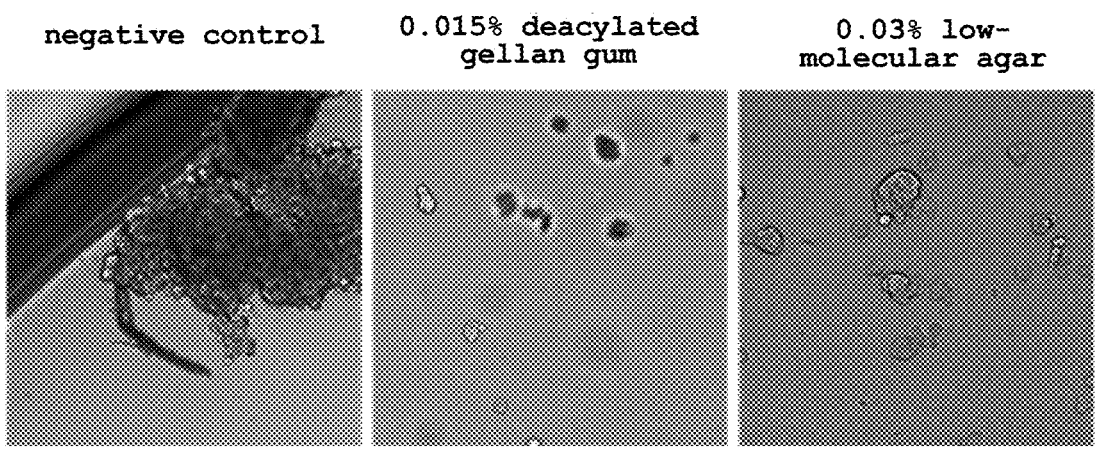
FIG. 8 shows observation images of A549 cells by a cell imaging apparatus in Experimental Example 5.

The observed images (area per 1 field: 1 $mm^2$) of A549 cells cultured for 10 days in the medium composition of the present invention containing low-molecular agar, negative control and comparison control (medium composition containing deacylated gellan gum) by a cell imaging apparatus are shown in FIG. 8. In addition, number of constituent cells of A549 cell spheres (average cell number per sphere), sphere number (average sphere number per 10 $mm^2$), projected area of sphere (size) ($µm^2$), obtained from the cell imaging analysis, are shown in Table 12. As for the negative control and comparison control, the relative cell number when the amount of luminescence without addition of the anticancer agent is 1 was determined from the measurement results of the surviving cell number using the intracellular ATP as an index, and shown in Table 13. Furthermore, the 50% inhibitory concentration (nM) of paclitaxel calculated from the amount of luminescence based on intracellular ATP and high content analysis are shown in Table 14.

TABLE 12

| paclitaxel addition concentration (µM) | average cell number per sphere | number of average spheres per 10 $mm^2$ | projected area ($µm^2$) |
|---|---|---|---|
| 0 | 5.04 | 32.66 | 1156 |
| 0.001 | 5.353 | 39.33 | 1161 |
| 0.01 | 1.52 | 18 | 578 |
| 0.1 | 1.165 | 6.333 | 402 |

TABLE 13

| paclitaxel addition concentration (µM) | relative cell number | |
|---|---|---|
| | negative control | comparison control |
| 0.001 | 1.004 | 0.842 |
| 0.01 | 0.249 | 0.156 |

TABLE 14

| analysis method/sample | cell survival assay by fluorescence | | high content analysis by cell image analysis |
|---|---|---|---|
| | negative control | comparison control | 0.03(w/v)% low-molecular agar |
| paclitaxel 50% inhibitory concentration (nM) | 4.4 | 2.9 | 1.9 |

From FIG. 8 and Tables 12, 14, it was confirmed that the number of constituent cells of the sphere formed from the cells, sphere number, and projected area (size) of sphere can be measured by high content analysis using the medium composition of the present invention. Furthermore, it was confirmed that an anticancer agent can be efficiently evaluated by high content analysis using the medium composition of the present invention. That is, when cultured in the medium composition of the present invention containing 0.03 (w/v) % low-molecular agar, since the cells are cultured in a uniformly dispersed state without floating, cell image analysis can be performed by performing a single centrifugation operation without diluting the cell culture, and the effect of anticancer agent could be rapidly and accurately evaluated.

On the other hand, in the negative control, since the cells are excessively coagulated near the wall of the wells, the cells were not within the area analyzable by the cell imaging apparatus. In addition, when cultured in the comparison control medium composition containing 0.015 (w/v) % deacylated gellan gum, since the cell did not fall on the bottom of the well by one centrifugation operation due to the cell floating ability of the deacylated gellan gum, focusing was not possible and the cell image analysis could not be performed.

[Experimental Example 6] Cell Proliferation Comparison Test with Agarose-Containing Medium Low-molecular agar ("ultra agar Ena", manufactured by Ina food Industry) was suspended in ultrapure water (Milli-Q water) at 2.0 (w/v) %, and dissolved by heating with stirring at 90° C. The aqueous solution was sterilized by an autoclave at 121° C. for 20 min. Using the aqueous solution, a medium composition containing 10 (v/v) % FBS and final concentration 0.03 (w/v) % of low-molecular agar in DMEM (manufactured by Wako Pure Chemical Industries, Ltd.) was prepared. Similarly, a medium composition containing 0.03 (w/v) % agarose ("Agarose S", manufactured by NIPPON GENE CO., LTD.), 0.1 (w/v) % low-melting point agarose ("Agarose, Low Gelation Temperature", manufactured by Sigma-Aldrich), and 0.07 (w/v) % fast-dissolving agar ("MAX", manufactured by InaFood Industry) was prepared.

The properties of the agarose, low-melting point agarose and fast-dissolving agar used in this Experimental Example are as described below.

(1) weight average molecular weight
agarose: about 220,000
(2) gel strength
(i) agarose: not less than 1,200 g/cm² by 1.5 (w/v) % gel
(ii) low-melting point agarose: not less than 200 g/cm² by 1.0 (w/v) % gel
(iii) fast-dissolving agar: 450±50 g/cm² by 1.5 (w/v) % gel
(3) melting point
(i) agarose: 1.5 (w/v) % aqueous solution, 88° C.-90° C.
(ii) low-melting point agarose: not more than 65° C.

Adenocarcinomic human alveolar basal epithelial cell line A549 (manufactured by DS PHARMA BIOMEDICAL CO., LTD.) was seeded in each of the above-mentioned medium compositions at 20,000 cells/mL, and dispensed to the wells of a 96 well flat bottom ultra-low attachment surface microplate (manufactured by Corning Incorporated, #3474) at 100 μL per 1 well. As the negative control, A549 cells were suspended in 10 (v/v) % FBS-containing DMEM and the suspension was dispensed. Successively, the microplate was cultured in a standing state in a $CO_2$ incubator (37° C., 5% $CO_2$) for 7 days. CellTiter-Glo Luminescent Cell Viability Assay (manufactured by Promega) (100 μL) was added to the cell culture medium after culturing for 2 days, 5 days and 7 days, stood for 10 min at room temperature, and the amount of luminescence was measured by a microplate reader ("FlexStation 3", manufactured by Molecular Devices) and according to the protocol recommended by Promega. The amount of luminescence of each medium alone was subtracted, whereby the number of viable cells was measured.

Figure 9:
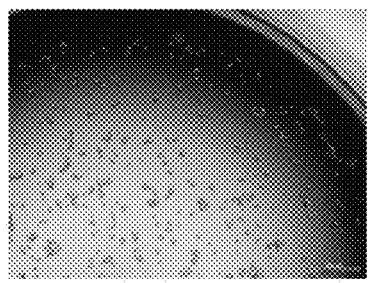
FIG. 9 shows the results of microscopic observation of a sphere of A549 cells after culturing for 7 days in Experimental Example 6.
Figure 9:
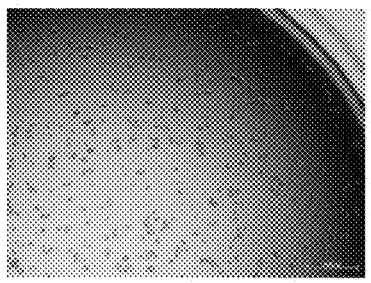
Figure 9:
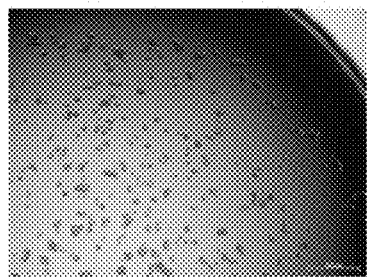
Figure 9:

The results of microscopic observation (instrument used: "inverted research microscope IX73" (manufactured by Olympus Corporation), magnification: ×40) of spheres of A549 cells after culturing for 7 days are shown in FIG. 9. In addition, the relative cell number when the amount of luminescence of the negative control is 1 was determined from the amount of luminescence (corresponding to the number of A549 cells) after stationary culture for 2 days, 5 days and 7 days, and shown in Table 15.

TABLE 15

| | | number of culturing days (days) | | |
|---|---|---|---|---|
| | | 2 | 5 | 7 |
| cell number | low-molecular agar 0.03(w/v)% | 1.172 | 3.214 | 3.831 |
| | agarose 0.03(w/v)% | 0.866 | 2.06 | 3.162 |
| | low-melting point agarose 0.1(w/v)% | 0.954 | 2.429 | 3.179 |
| | Fast-dissolving agar 0.07(w/v)% | 1.041 | 2.741 | 3.547 |

As shown in FIG. 9, using medium compositions containing the above-mentioned low-molecule or fast-dissolving agar, or each of the above-mentioned agaroses, A549 cells were found to proliferate well in a dispersed state. As shown in Table 15, moreover, a good proliferation promoting effect was found in any medium composition used, as compared to the negative control, and the highest promotion of proliferation was found in the medium composition containing low-molecular agar.

[Experimental Example 7] Cell Proliferation Test of Spheres Using Mixed Agent of Various Polysaccharides By a method similar to Experimental Example 3, medium compositions respectively containing 0.015 (w/v) % of low-molecular agar ("ultra agar Ena", manufactured by Ina Food Industry) and 0.05 (w/v) % of xanthan gum ("KELTROL CG", manufactured by Shansho Co., Ltd.), 0.03 (w/v) % of the aforementioned low-molecular agar and 0.05 (w/v) % of κ-carrageenan ("GENUGEL WR-80-J", manufactured by Shansho Co., Ltd.), and 0.03 (w/v) % of the aforementioned low-molecular agar and 0.005 (w/v) % of deacylated gellan gum ("KELCOGEL CG-LA", manufactured by Shansho Co., Ltd.) in DMEM added with 10 (v/v) % FBS were prepared.

Adenocarcinomic human alveolar basal epithelial cell line A549 (manufactured by DS PHARMA BIOMEDICAL CO., LTD.) was seeded in each of the above-mentioned medium compositions at 20,000 cells/mL, and dispensed to the wells of a 96 well flat bottom ultra-low attachment surface microplate (manufactured by Corning Incorporated, #3474) at 100 μL per 1 well. As a negative control, A549 cells were suspended in DMEM added with 10 (v/v) % FBS and the suspension was dispensed.

Successively, the plate was cultured in a standing state in a $CO_2$ incubator (37° C., 5% $CO_2$) for 7 days. CellTiter-Glo Luminescent Cell Viability Assay (manufactured by Promega) (100 μL) was added to each cell culture media after culturing for 2 days, 5 days, 7 days, the mixture was stood for 10 min at room temperature, and the amount of luminescence was measured by a microplate reader ("FlexStation 3", manufactured by Molecular Devices) and according to the protocol recommended by Promega. The amount of luminescence of each medium alone was subtracted, whereby the number of viable cells was measured.

Figure 10:
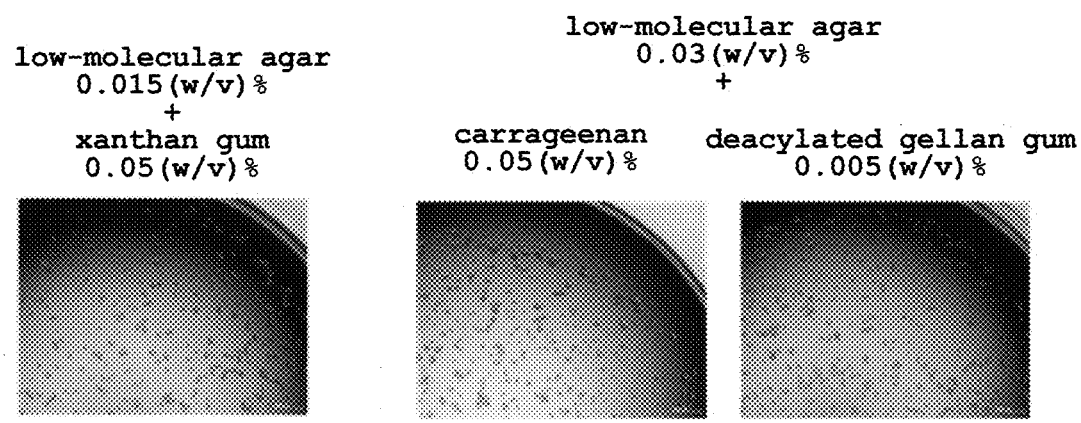
FIG. 10 shows the results of microscopic observation of a sphere of A549 cells after culturing for 7 days in Experimental Example 7.

The results of microscopic observation (instrument used: "inverted research microscope IX73" (manufactured by Olympus Corporation), magnification: ×40) of spheres of A549 cells after culturing for 7 days are shown in FIG. 10. Furthermore, the relative cell number when the amount of luminescence of the negative control is 1 was determined from the amount of luminescence (corresponding to the number of A549 cells) after stationary culture for 2 days, 5 days and 7 days, and shown in Table 16.

TABLE 16

| | low-molecular agar concentration [(w/v) %] | polysaccharide concentration [(w/v) %] | culturing days (days) | | |
|---|---|---|---|---|---|
| | | | 2 | 5 | 7 |
| cell number | 0.015 | xanthan gum 0.05 | 1.281 | 3.854 | 4.954 |
| | 0.03 | κ-carrageenan 0.05 | 1.095 | 2.522 | 3.87 |
| | 0.03 | deacylated gellan gum 0.005 | 1.173 | 3.048 | 3.555 |

As shown in FIG. 10, it was shown that A549 cells proliferate by dispersing well in the medium composition containing low-molecular agar and various polysaccharides.

As shown in Table 16, moreover, culturing in a medium composition containing low-molecular agar and various polysaccharides afforded a good cell proliferation promoting effect.

[Experimental Example 8] High Content Analysis Using Medium Containing Low-Molecular Agar By a method similar to the preparation method of medium composition of Experimental Example 1, a medium composition containing 10 (v/v) % FBS and 0.03 (w/v) % of low-molecular agar ("ultra agar Ena", manufactured by Ina Food Industry) in DMEM (manufactured by Wako Pure Chemical Industries, Ltd.) was prepared.

Adenocarcinomic human alveolar basal epithelial cell line A549 (manufactured by DS PHARMA BIOMEDICAL CO., LTD.) was suspended in the above-mentioned medium composition containing low-molecular agar at 11,000 cells/mL. The above-mentioned cell suspension was dispensed to the wells of a 96 well flat bottom ultra-low attachment surface microplate (manufactured by Corning Incorporated, #3474) at 90 μL per 1 well. The plate was stood in a $CO_2$ incubator (37° C., 5% $CO_2$) overnight. The next day, paclitaxel (manufactured by Wako Pure Chemical Industries, Ltd.) and trametinib (manufactured by SANTA CRUZ) were further added by 10 μl per 1 well at a final concentration of 0.001 μM, 0.01 μM and 0.1 μM, respectively, mitomycin C (manufactured by Wako Pure Chemical Industries, Ltd.) at a final concentration of 0.005 μM, 0.05 μM and 0.5 μM, and MK2206 (manufactured by SANTA CRUZ) at a final concentration of 0.001 μM, 0.01 μM, 0.1 μM and 1 μM. Successively, the plate was further cultured in a standing state in a $CO_2$ incubator (37° C., 5% $CO_2$) for 7 days.

As a negative control, a medium composition containing 10 (v/v) % FBS alone in DMEM (manufactured by Wako Pure Chemical Industries, Ltd.) was prepared. As a comparison target, similar to Experimental Example 3, medium composition containing 10 (v/v) % FBS and 0.015 (w/v) % of deacylated gellan gum in DMEM (manufactured by Wako Pure Chemical Industries, Ltd.) was prepared. A549 cells were also suspended in each of the negative control and comparison control medium compositions, the negative control was dispensed to a 96 well flat bottom attachment surface microplate (manufactured by Corning Incorporated, #3585) and the comparison control was dispensed to a 96 well flat bottom ultra-low attachment surface microplate (manufactured by Corning Incorporated, #3474). The next day, each anticancer agent was added at the above-mentioned concentration, successively, the plate was further cultured in a standing state in a $CO_2$ incubator (37° C., 5% $CO_2$) for 7 days.

Then, a solution of 200 mg/mL of Hoechst 33342 (manufactured by Invitrogen) in DMEM (phenol red, L-glutamine free) (manufactured by Wako Pure Chemical Industries, Ltd.) was prepared, and added, at 10 μL per 1 well, to the culture in the above-mentioned low-molecular agar-containing medium after static culture for 8 days, and the mixture was stood in a $CO_2$ incubator (37° C., 5% $CO_2$) for 45 min. Successively, a solution of 20 μg/mL Propidium Iodide (manufactured by BIOMOL) in DMEM (phenol red, L-glutamine free) (manufactured by Wako Pure Chemical Industries, Ltd.) was prepared and added at 10 μL per 1 well, and the culture medium was suspended. The plate was centrifuged at 1,500 rpm for 1 min, and high content analysis was performed by cell image analysis using a cell imaging apparatus ("ArrayScan VTI HCS Reader", manufactured by Thermo Fisher Scientific). At that time, observation was performed with 20 fields of view per well using a ×10 objective lens, cell outline and cell nucleus were detected from Hoechst33342 fluorescence image, and dead cells were detected from propidium iodide fluorescence image. In addition, 50% inhibitory concentration (nM) of each anticancer agent by high content analysis was calculated from the number of spheres constituted of not less than 5 cells. In this case, the value without addition of the anticancer agent was taken as 0% sphere formation inhibitory rate.

CellTiter-Glo Luminescent Cell Viability Assay (manufactured by Promega) (100 μL) was added to the low-molecular agar-containing culture medium and each cell culture medium of the negative control and comparison control, the mixture was stood for 10 min at room temperature, and the amount of luminescence was measured by a microplate reader ("FlexStation 3", manufactured by Molecular Devices) and according to the protocol recommended by Promega. The amount of luminescence of the medium alone was subtracted, whereby the number of viable cells was measured. In addition, 50% inhibitory concentration (nM) of an anticancer agent by the amount of luminescence was calculated with the number of viable cells when the anticancer agent was not added as 0% inhibition rate.

The number of constituent cells of A549 cell spheres (average cell number per sphere), sphere number (average sphere number per 20 mm$^2$), projected area of sphere (size) ($\mu m^2$) and the average dead cell number in the sphere, obtained from the cell imaging analysis, are shown in Tables 17-20. Furthermore, the relative cell number when the amount of luminescence without addition of the anticancer agent is 100 was determined from the measurement results of the surviving cell number using the intracellular ATP as an index, and shown in Tables 21-24. In addition, the 50% inhibitory concentration (nM) of an anticancer agent calculated from the amount of luminescence based on intracellular ATP and high content analysis are shown in Table 25.

TABLE 17

| paclitaxel addition concentration ($\mu M$) | average cell number per sphere | average sphere number per 20 mm$^2$ | projected area ($\mu m^2$) | average dead cell number in sphere |
|---|---|---|---|---|
| 0 | 4.464 | 343.3 | 1208 | 0.029 |
| 0.001 | 4.817 | 297.7 | 1271 | 0.064 |
| 0.01 | 2.3 | 187 | 797 | 0.336 |
| 0.1 | 1.662 | 133 | 647 | 0.591 |

TABLE 18

| trametinib addition concentration ($\mu M$) | average cell number per sphere | average sphere number per 20 mm$^2$ | projected area ($\mu m^2$) | average dead cell number in sphere |
|---|---|---|---|---|
| 0 | 4.476 | 244.9 | 1248 | 0.038 |
| 0.001 | 4.272 | 218.7 | 1200 | 0.073 |
| 0.01 | 2.906 | 173.9 | 976.6 | 0.09 |
| 0.1 | 1.867 | 132.8 | 618.3 | 0.178 |

TABLE 19

| mitomycin C addition concentration ($\mu M$) | average cell number per sphere | average sphere number per 20 mm$^2$ | projected area ($\mu m^2$) | average dead cell number in sphere |
|---|---|---|---|---|
| 0 | 4.962 | 321.1 | 1398 | 0.077 |
| 0.005 | 3.72 | 265.2 | 1139 | 0.151 |
| 0.05 | 2.187 | 190.6 | 810.7 | 0.33 |
| 0.5 | 1.447 | 113.3 | 460.8 | 0.606 |

TABLE 20

| MK2206 addition concentration ($\mu M$) | average cell number per sphere | average sphere number per 20 mm$^2$ | projected area ($\mu m^2$) | average dead cell number in sphere |
|---|---|---|---|---|
| 0 | 4.917 | 223.2 | 1376 | 0.086 |
| 0.001 | 5.044 | 230.6 | 1361 | 0.104 |
| 0.01 | 4.774 | 213.7 | 1343 | 0.074 |
| 0.1 | 4.323 | 206.1 | 1199 | 0.076 |
| 1 | 3.423 | 142.3 | 931.2 | 0.332 |

TABLE 21

| paclitaxel addition concentration ($\mu M$) | low-molecular agar-containing medium | negative control | comparison control |
|---|---|---|---|
| 0.001 | 102.4 | 100.1 | 99.9 |
| 0.01 | 27 | 18.8 | 23.5 |
| 0.1 | 12.1 | 5.5 | 10.8 |

TABLE 22

| trametinib addition concentration ($\mu M$) | low-molecular agar-containing medium | negative control | comparison control |
|---|---|---|---|
| 0.001 | 92.2 | 101.2 | 93.3 |
| 0.01 | 45.8 | 99 | 52.5 |
| 0.1 | 18.2 | 37.4 | 18.1 |

TABLE 23

| mitomycin addition concentration ($\mu M$) | low-molecular agar-containing medium | negative control | comparison control |
|---|---|---|---|
| 0.005 | 59.5 | 94 | 62.8 |
| 0.05 | 27.8 | 55.9 | 29.5 |
| 0.5 | 8.1 | 12.3 | 8.6 |

TABLE 24

| MK2206 addition concentration ($\mu M$) | low-molecular agar-containing medium | negative control | comparison control |
|---|---|---|---|
| 0.001 | 100.1 | 100.2 | 95.8 |
| 0.01 | 93.9 | 101.3 | 89.1 |
| 0.1 | 66.5 | 97.6 | 61.8 |
| 1 | 25.7 | 95.7 | 25.2 |

TABLE 25

| analysis method/sample | | cell survival assay by luminescence | | | high content analysis by cell image analysis |
|---|---|---|---|---|---|
| | | low-molecular agar-containing medium | negative control | compare-son control | low-molecular agar-containing medium |
| 50% inhibitory concentration (nM) | paclitaxel | 4.9 | 4.1 | 4.5 | 4.1 |
| | trametinib | 8.1 | 62.5 | 11.5 | 5.1 |
| | mitomycin C | 10 | 71.4 | 12.1 | 6.4 |
| | MK2206 | 250 | 1000 | 210 | 210 |

From Tables 17-25, it was confirmed that the number of constituent cells of the sphere formed from the cells, sphere number, projected area (size) of sphere and dead cell number in the sphere can be measured by high content analysis using the medium composition of the present invention.

Furthermore, it was confirmed that an anticancer agent can be efficiently evaluated by high content analysis using the medium composition containing low-molecular agar of the present invention. That is, when cultured in the medium composition of the present invention containing 0.03 (w/v) % low-molecular agar, since the cells are cultured in a uniformly dispersed state without floating, cell image analysis can be performed by performing a single centrifugation operation without diluting the cell culture, and the effect of anticancer agent could be rapidly and accurately evaluated.

On the other hand, in the negative control, since the cells are excessively coagulated near the wall of the wells, the cells were not within the area analyzable by the cell imaging apparatus. In addition, when cultured in the comparison control medium composition containing 0.015 (w/v) % deacylated gellan gum, since the cell did not fall on the bottom of the well by one centrifugation operation due to the cell floating ability of the deacylated gellan gum, focusing was not possible and the cell image analysis could not be performed.

[Experimental Example 9] Evaluation of Hepatotoxic Substance Using Low-Molecular Agar-Containing Medium By a method similar to the preparation method of medium composition of Experimental Example 1, a medium composition containing 10 (v/v) % FBS and 0.03 (w/v) % of low-molecular agar ("ultraagar Ena", manufactured by Ina-Food Industry) in DMEM (manufactured by Wako Pure Chemical Industries, Ltd.) was prepared. Human liver cancer cell line HepG2 (manufactured by DS PHARMA BIOMEDICAL CO., LTD.) was suspended in the above-mentioned medium composition containing low-molecular agar at 11,000 cells/mL. The above-mentioned cell suspension was dispensed to the wells of a 96 well flat bottom ultra-low attachment surface microplate (manufactured by Corning Incorporated, #3474) at 90 μL per 1 well, and the plate was cultured in a standing state in a $CO_2$ incubator (37° C., 5% $CO_2$) for 3 days. On day 3 of culture, flutamide (manufactured by Sigma-Aldrich) was added by 10 μL per 1 well. Successively, the plate was further cultured in a standing state in a $CO_2$ incubator (37° C., 5% $CO_2$) for 2 days. As a comparison control, HepG2 cells were suspended in DMEM containing 10 (v/v) % FBS and the suspension was dispensed to a 96 well flat bottom adhesion surface microplate (manufactured by Corning Incorporated, #3585), and a similar operation was performed.

Then, a solution of 200 mg/mL of Hoechst 33342 (manufactured by Invitrogen) in DMEM (phenol red, L-glutamine free) (manufactured by Wako Pure Chemical Industries, Ltd.) was prepared, and added, at 10 μL per 1 well, to each culture after static culture for 5 days using the above-mentioned low-molecular agar-containing medium and comparison control, and the mixture was stood in a $CO_2$ incubator (37° C., 5% $CO_2$) for 45 min. Successively, a solution of 20 μg/mL Propidium Iodide (manufactured by BIOMOL) in DMEM (phenol red, L-glutamine free) (manufactured by Wako Pure Chemical Industries, Ltd.) was prepared and added at 10 μL per 1 well, and the culture medium was suspended. The plate was centrifuged at 1,500 rpm for 1 min, and high content analysis was performed by cell image analysis using a cell imaging apparatus ("Array-Scan VTI HCS Reader", manufactured by Thermo Fisher Scientific). At that time, observation was performed with 20 fields of view per well using a ×10 objective lens, cell outline and cell nucleus were detected from Hoechst33342 fluorescence image, and dead cells were detected from propidium iodide fluorescence image. In addition, 50% inhibitory concentration (μM) of flutamide by high content analysis was calculated from the number of cells constituting the spheres, with the value without addition of flutamide as 0% sphere formation inhibitory rate.

CellTiter-Glo Luminescent Cell Viability Assay (manufactured by Promega) (100 μL) was added to the low-molecular agar-containing culture medium and comparison control, the mixture was stood for 10 min at room temperature, and the amount of luminescence was measured by a microplate reader ("FlexStation 3", manufactured by Molecular Devices) and according to the protocol recommended by Promega. The amount of luminescence of the medium alone was subtracted, whereby the number of viable cells was measured. In addition, 50% inhibitory concentration (μM) of flutamide by the amount of luminescence was calculated with the number of viable cells when flutamide was not added as 0% inhibition rate.

The number of constituent cells of HepG2 cell spheres, sphere number, projected area of sphere (size) (μm$^2$) and the dead cell number in the sphere, obtained from the cell imaging analysis, are shown in Table 26. Furthermore, the relative cell number when the amount of luminescence without addition of the anticancer agent is 100 was determined from the measurement results of the surviving cell number by luminescence, using the intracellular ATP as an index, and shown in Table 27. In addition, the 50% inhibitory concentration (μM) of flutamide calculated from the amount of luminescence based on intracellular ATP and constituent cell number obtained by high content analysis are shown in Table 28.

TABLE 26

| flutamide addition concentration (μM) | average cell number per sphere | average sphere number per 20 mm$^2$ | projected area (μm$^2$) | average dead cell number in sphere |
|---|---|---|---|---|
| 0 | 9.637 | 230.3 | 2326 | 0.043 |
| 0.8 | 7.977 | 190.7 | 1988 | 0.06 |
| 4 | 8.89 | 145.3 | 2180 | 0.037 |
| 20 | 9.263 | 129.7 | 2403 | 0.067 |

TABLE 26-continued

| flutamide addition concentration (μM) | average cell number per sphere | average sphere number per 20 mm² | projected area (μm²) | average dead cell number in sphere |
|---|---|---|---|---|
| 100 | 3.76 | 153.7 | 861 | 0.007 |
| 500 | 1.567 | 7.3 | 408 | 1.163 |

TABLE 27

| flutamide addition concentration (μM) | low-molecular agar-containing medium | comparison control |
|---|---|---|
| 0.8 | 109.6 | 100.2 |
| 4 | 98.7 | 109.6 |
| 20 | 89.8 | 93.5 |
| 100 | 22.4 | 22.5 |
| 500 | 8.1 | 15.4 |

TABLE 28

| analysis method/ sample | | cell survival assay by luminescence | | high content analysis by cell image |
|---|---|---|---|---|
| | | low-molecular agar containing medium | comparison control | analysis low-molecular agar-containing medium |
| 50% inhibitory concentration (μM) | flutamide | 53.6 | 51.7 | 73.4 |

From the results shown in Tables 26-28, it was confirmed that the hepatotoxicity of flutamide can be evaluated using high content analysis by cell image analysis, by culturing cells using the medium composition of the present invention containing low-molecular agar.

[Experimental Example 10] Dispersibility Test Using Filter-Filtered Medium Composition Preparation of Low-Molecular Agar-Containing Medium Composition Low-molecular agar ("ultra agar Ena", manufactured by Ina Food Industry) was suspended in ultrapure water (Milli-Q water) at 1.0 (w/v) %, and dissolved by heating with stirring at 90° C. The aqueous solution was stirred, and completely dissolved by autoclave sterilization at 121° C. for 20 min. The mixture was allowed to cool to room temperature, and the gelated aqueous low-molecular agar solution was redissolved by heating in a microwave oven. The aqueous solution (150 μL) was placed in a 15 mL centrifuge tube (manufactured by AS ONE Corporation), DMEM (manufactured by Wako Pure Chemical Industries, Ltd.) (9.85 mL) heated to 37° C. was added, and the mixture was quickly stirred, whereby a medium composition having a final concentration of low-molecular agar of 0.03 (w/v) % was prepared. This medium composition was placed under the 4 conditions shown in Table 29, and filtered through pore size 70 μm filter and 40 μm filter (manufactured by BD Falcon), 30 μm filter and 20 μm filter (manufactured by AS ONE Corporation), 10 μm filter (manufactured by Partec), and 5 μm filter, 1.2 μm filter, 0.45 μm filter and 0.2 μm filter (manufactured by Sartorius Stedim Japan). In this case, the filtrate was set to at least 2 mL.

TABLE 29

| conditions | preservation conditions after low-molecular agar addition | with or without FBS addition | temperature of medium composition during filtration |
|---|---|---|---|
| (1) | room temperature for 1 hr | none | room temperature |
| (2) | room temperature for 1 hr | yes | room temperature |
| (3) | 4° C. for 24 hr | none | 4° C. |
| (4) | 4° C. for 24 hr | none | 37° C. |

FBS was added to the above-mentioned filtrate such that FBS-free filtrate has a final concentration of 10 (v/v) %, adenocarcinomic human alveolar basal epithelial cell line A549 (manufactured by DS PHARMA BIOMEDICAL CO., LTD.) was seeded at 10,000 cells/mL, and dispensed to the wells of a 96-well flat bottom ultra-low attachment surface microplate (manufactured by Corning Incorporated, #3474) to 100 μL/well. As a negative control, A549 cells were suspended in the above-mentioned medium free of low-molecular agar, and as a positive control, A549 cells were suspended in the above-mentioned medium containing low-molecular agar and free of filter filtration, and the suspensions were dispensed. Successively, the plate was cultured in a standing state in a $CO_2$ incubator (37° C., 5% $CO_2$) for 7 days. The dispersion state of the cells was visually observed 7 days later. The dispersion state was evaluated by "○ dispersed well", "Δ; partly coagulated", "x; remarkably coagulated", and the results are shown in Table 30.

TABLE 30

| pore size (μm) of filter | with or without low-molecular agar addition | preservation conditions of medium after low-molecular agar addition | | | |
|---|---|---|---|---|---|
| | | (1) | (2) | (3) | (4) |
| negative control | − | x | x | x | x |
| positive control | + | ○ | ○ | ○ | ○ |
| 0.2 | | ○ | ○ | x | x |
| 0.45 | | ○ | ○ | x | x |
| 1.2 | | ○ | ○ | Δ | Δ |
| 5 | | ○ | ○ | ○ | ○ |
| 10 | | ○ | ○ | ○ | ○ |
| 20 | | ○ | ○ | ○ | ○ |
| 30 | | ○ | ○ | ○ | ○ |
| 40 | | ○ | ○ | ○ | ○ |
| 70 | | ○ | ○ | ○ | ○ |

As shown in Table 30, in a medium composition obtained by adding low-molecular agar, preserving the medium composition at room temperature for 1 hr, and passing through a filter with a pore size of not less than 0.2 μm, A549 cell spheres were maintained well in a dispersed state. On the other hand, in a medium composition obtained by adding low-molecular agar, preserving the medium composition at 4° C., and filtering same with a filter under both 4° C. and 37° C. conditions, sphere of A549 cells were maintained well in a dispersed state when the pore size of the filter was not less than 5 μm. It was confirmed, however, when the pore size of the filter was 1.2 μm, A549 cell spheres were partly coagulated, and when the pore size of the filter was not more than 0.45 μm, A549 cells sphere were coagulated.

The above results suggest that the size of the coagulation structure of low-molecular agar contained in the medium composition is about 0.45 μm to 5 μm.

[Experimental Example 11] Sphere Formation Assay

By a method similar to the preparation method of medium composition of Experimental Example 1, a medium composition containing 10 (v/v) % FBS and 0.03 (w/v) % of low-molecular agar ("ultra agar Ena", manufactured by Ina Food Industry) in DMEM (manufactured by Wako Pure Chemical Industries, Ltd.) was prepared. Human uterus cervix cancer cell line HeLa (manufactured by DS PHARMA BIOMEDICAL CO., LTD.) was suspended at 5,000 cells/mL in the above-mentioned medium composition containing low-molecular agar. The above-mentioned cell suspension was dispensed to the wells of a 96-well flat bottom ultra-low attachment surface microplate (manufactured by Corning Incorporated, #3474) to 100 μL/well per 1 well and the plate was cultured in a $CO_2$ incubator (37° C., 5% $CO_2$) for 21 days at the longest. As a negative control, HeLa cells were suspended in the above-mentioned medium free of low-molecular agar, and the suspension was dispensed. The results of microscopic observation (instrument used: "inverted research microscope IX73" (manufactured by Olympus Corporation), magnification: ×40) of the state of HeLa cells on day 21 of culture are shown in FIG. 11.

Figure 11:
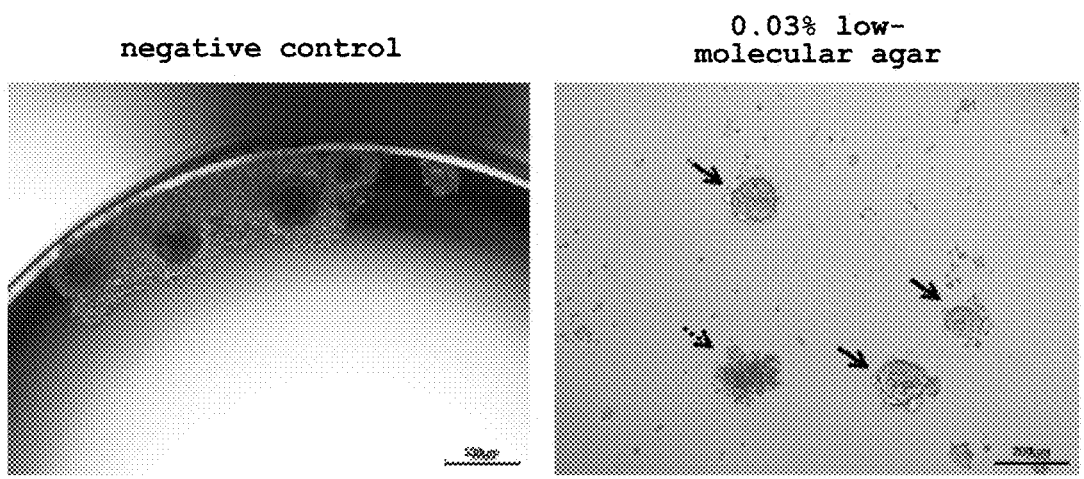
FIG. 11 shows the results of microscopic observation of a sphere of HeLa cells after culturing for 21 days in Experimental Example 11. In the Figure, solid arrows show hard and spherically coagulated spheres, and dotted arrows show loosely coagulated spheres.

As shown in FIG. 11, in the negative control in which cells were cultured in a medium not containing low-molecular agar, it was observed that seeded HeLa cells gathered on the edge of the well and were over-aggregated, and sphere formability of each cell could not be evaluated. On the other hand, when the cells were cultured in a medium containing 0.03 (w/v) % of low-molecular agar, over-aggregation of HeLa cells was suppressed. In FIG. 11, formation of not only hard and spherically coagulated spheres shown with a solid line arrow, but also loosely coagulated spheres shown with a dotted line arrow was observed.

From the above, it was confirmed that sphere formation assay for evaluation of the proliferation property and stem cell property of each cell can be performed by culturing cells in the medium composition of the present invention.

INDUSTRIAL APPLICABILITY

As described in detail in the above, the present invention can provide a medium additive, a medium composition and a culture method capable of culturing cells or tissues in a dispersed state in any of a floating state and a precipitated state.

The medium additive, medium composition and culture method of the present invention can be preferably used for culturing adherent cells adhered to a carrier surface or embedded in a carrier inside, or adherent cells forming a sphere.

Using the medium additive or medium composition of the present invention, moreover, since cultured product can be quickly analyzed by cell image analysis, the present invention can be preferably used for screening for a pharmaceutical product candidate substance for anticancer agent and the like.

This application is based on patent application Nos. 2015-84590 and 2015-229974 filed in Japan, the contents of which are incorporated in full herein.

The invention claimed is:

1. A method of culturing a cell or tissue, comprising cultivating the cell or tissue in a precipitated state on the bottom of a culture container but in a dispersed state in a medium composition comprising agar having a weight average molecular weight of 10,000-60,000,
    wherein the agar is present in the medium composition in an amount of not less than 0.005 (w/v)% and less than 0.07 (w/v)% relative to the total amount of the medium composition, and
    wherein the medium composition has a viscosity at 37° C. of not more than 2.5 mPa·s when the agar content is 0.1 (w/v)%.

2. The method according to claim 1, wherein the cell is an adherent cell or a floating cell.

3. The method according to claim 2, wherein the adherent cell is adhered to a carrier surface or embedded inside a carrier.

4. The method according to claim 2, wherein the adherent cell is adhered to a microcarrier.

5. The method according to claim 2, wherein the adherent cell forms a sphere.

6. The method according to claim 2, wherein the adherent cell is selected from the group consisting of a cancer cell, a hepatocyte and a cancer cell line.

* * * * *